US009459269B2

(12) United States Patent
Cohen

(10) Patent No.: US 9,459,269 B2
(45) Date of Patent: Oct. 4, 2016

(54) ASSAY TIMING IN A CLINICAL ANALYZER USING A CUVETTE CARRIER

(75) Inventor: Beri J. Cohen, Hartsdale, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1531 days.

(21) Appl. No.: 11/915,870

(22) PCT Filed: Jul. 21, 2006

(86) PCT No.: PCT/US2006/028144
§ 371 (c)(1),
(2), (4) Date: Nov. 29, 2007

(87) PCT Pub. No.: WO2007/013960
PCT Pub. Date: Feb. 1, 2007

(65) Prior Publication Data
US 2009/0308183 A1    Dec. 17, 2009

Related U.S. Application Data

(60) Provisional application No. 60/702,036, filed on Jul. 22, 2005.

(51) Int. Cl.
*G01N 35/02* (2006.01)
*G01N 35/10* (2006.01)
*G01N 35/00* (2006.01)

(52) U.S. Cl.
CPC ...... *G01N 35/0092* (2013.01); *G01N 35/0098* (2013.01); *G01N 35/026* (2013.01); *G01N 2035/0093* (2013.01); *G01N 2035/0094* (2013.01)

(58) Field of Classification Search
CPC .................................. G01N 35/0092–35/0094
See application file for complete search history.

(56) References Cited

U.S. PATENT DOCUMENTS 5,576,215 A    11/1996  Burns et al.
5,599,501 A *  2/1997  Carey et al. .................... 422/64
(Continued)

FOREIGN PATENT DOCUMENTS

JP    57044855    3/1982
JP    62121364    6/1987
(Continued)

OTHER PUBLICATIONS

Supplementary European Search Report dated Apr. 29, 2014 of corresponding European Patent Application No. 06800147.8, 5 Pages.

*Primary Examiner* — P. Kathryn Wright

(57) ABSTRACT

The clinical analyzer includes a cuvette carrier that is moved in a manner to provide flexible assay timing and variable incubation periods. Multiple assays having such varied incubation times can be run concurrently in random-access, avoiding timing conflicts. Fluid delivery stations are placed around the cuvette carrier in positions that are independent of assay timing. The cuvettes move in unison, in multiples of incremental steps, along a closed geometrical path. The cuvette carrier is movable variable distances in opposite directions in a single time cycle to position specific cuvettes at specific locations for delivery of sample or reagent. The direction of movement of the cuvette carrier is preferably based on a determination of the shortest distance between the cuvette and respective fluid delivery stations. However, in each time cycle there is a net progressive incremental stepwise movement of the cuvettes in a selected direction.

21 Claims, 22 Drawing Sheets

(56) References Cited

U.S. PATENT DOCUMENTS

| | | | |
|---|---|---|---|
| 5,846,491 A * | 12/1998 | Choperena et al. | 422/67 |
| 2003/0040117 A1 * | 2/2003 | Devlin, Sr. | 436/46 |
| 2003/0054557 A1 | 3/2003 | Devlin, Sr. | |
| 2005/0220670 A1 * | 10/2005 | Palmieri et al. | 422/64 |

FOREIGN PATENT DOCUMENTS

| | | |
|---|---|---|
| JP | 2004522979 | 7/2004 |
| WO | 97/22006 A1 | 6/1997 |
| WO | 03012454 | 2/2003 |

\* cited by examiner

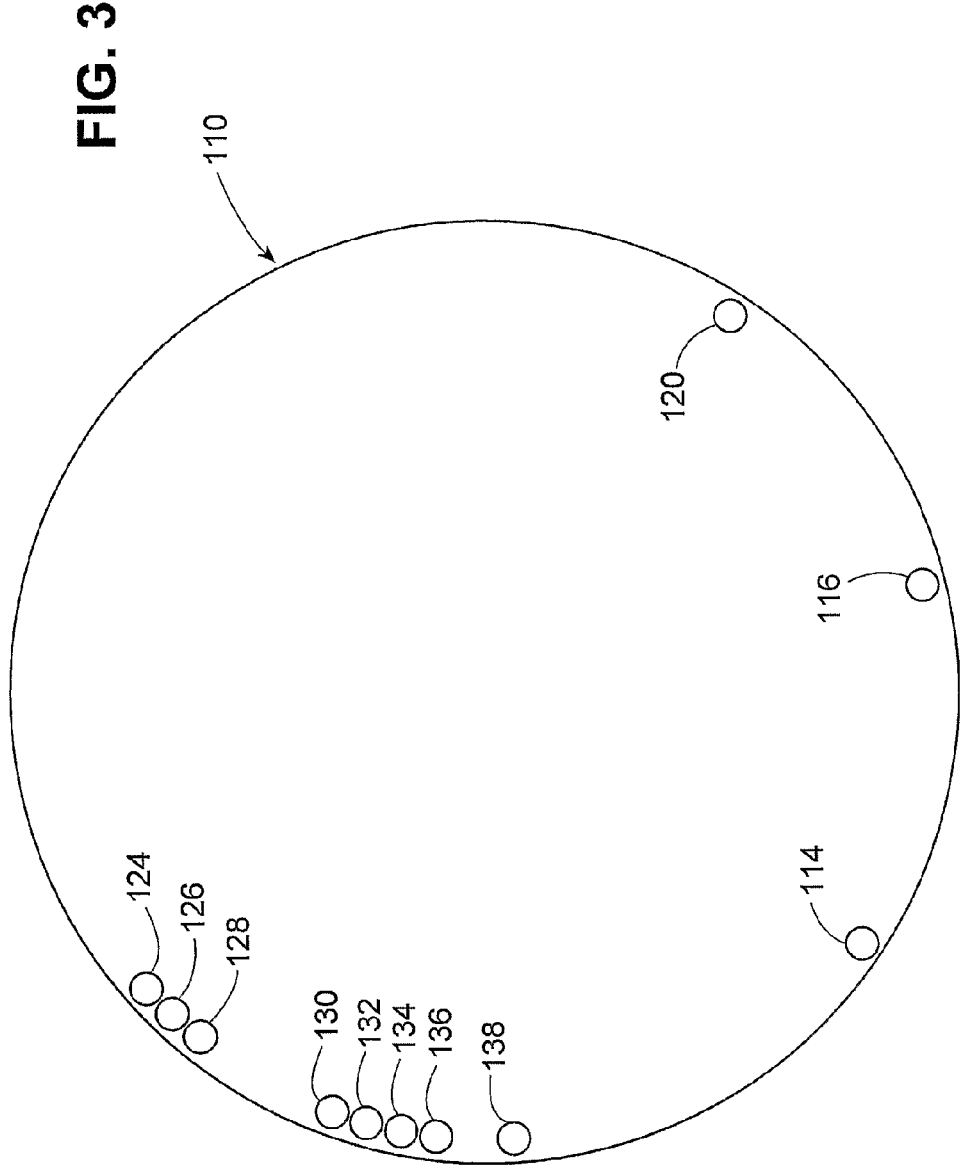

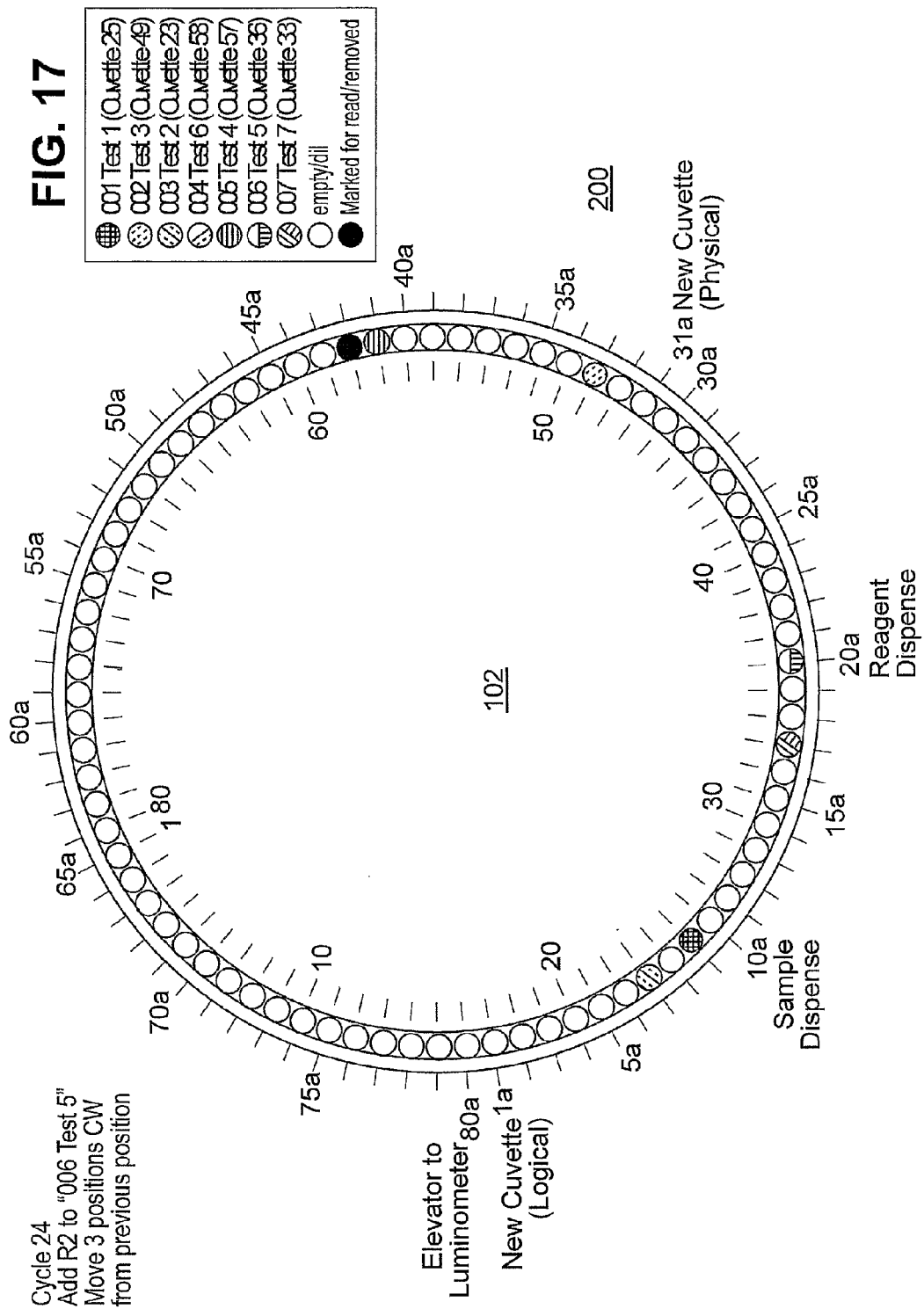

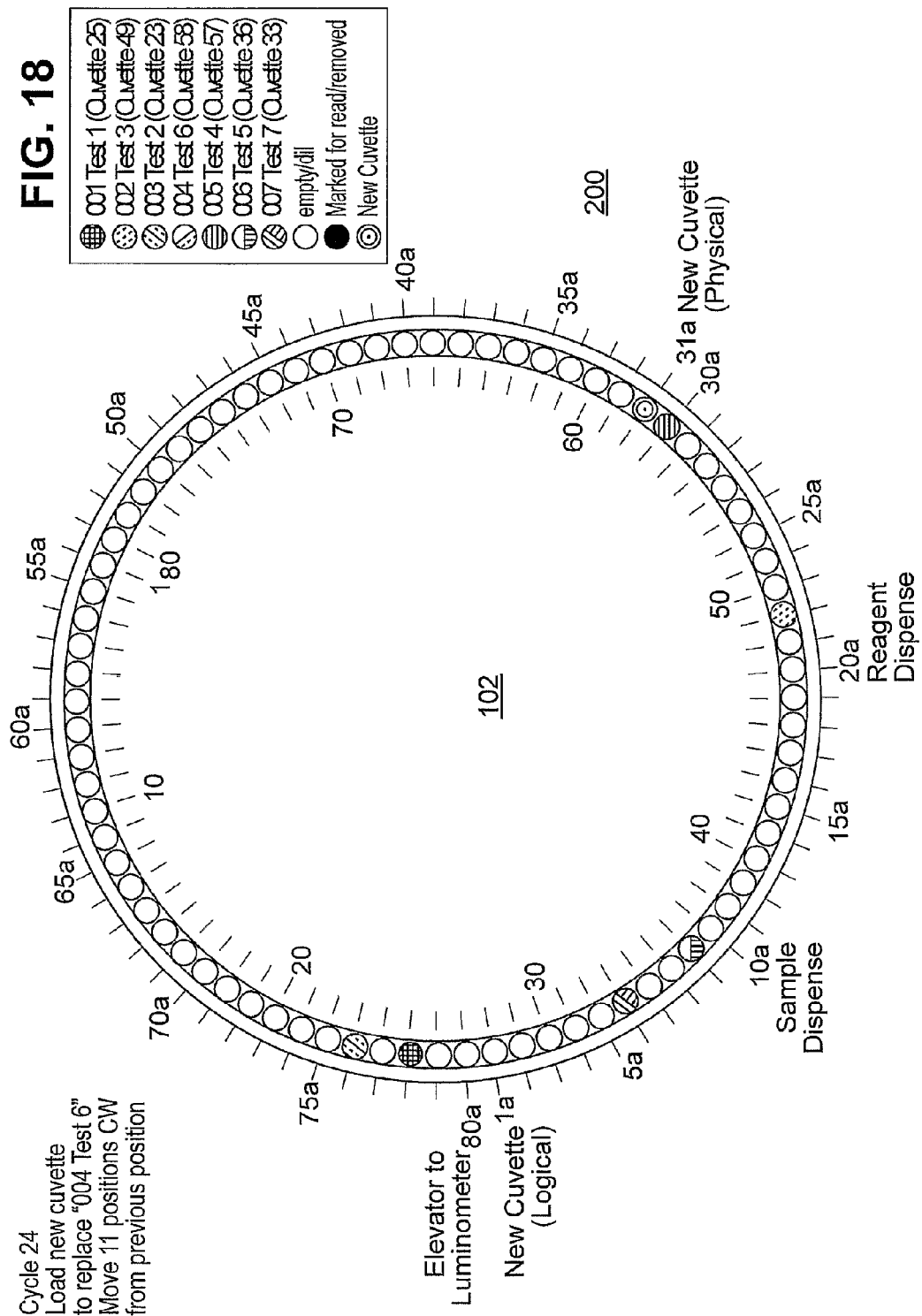

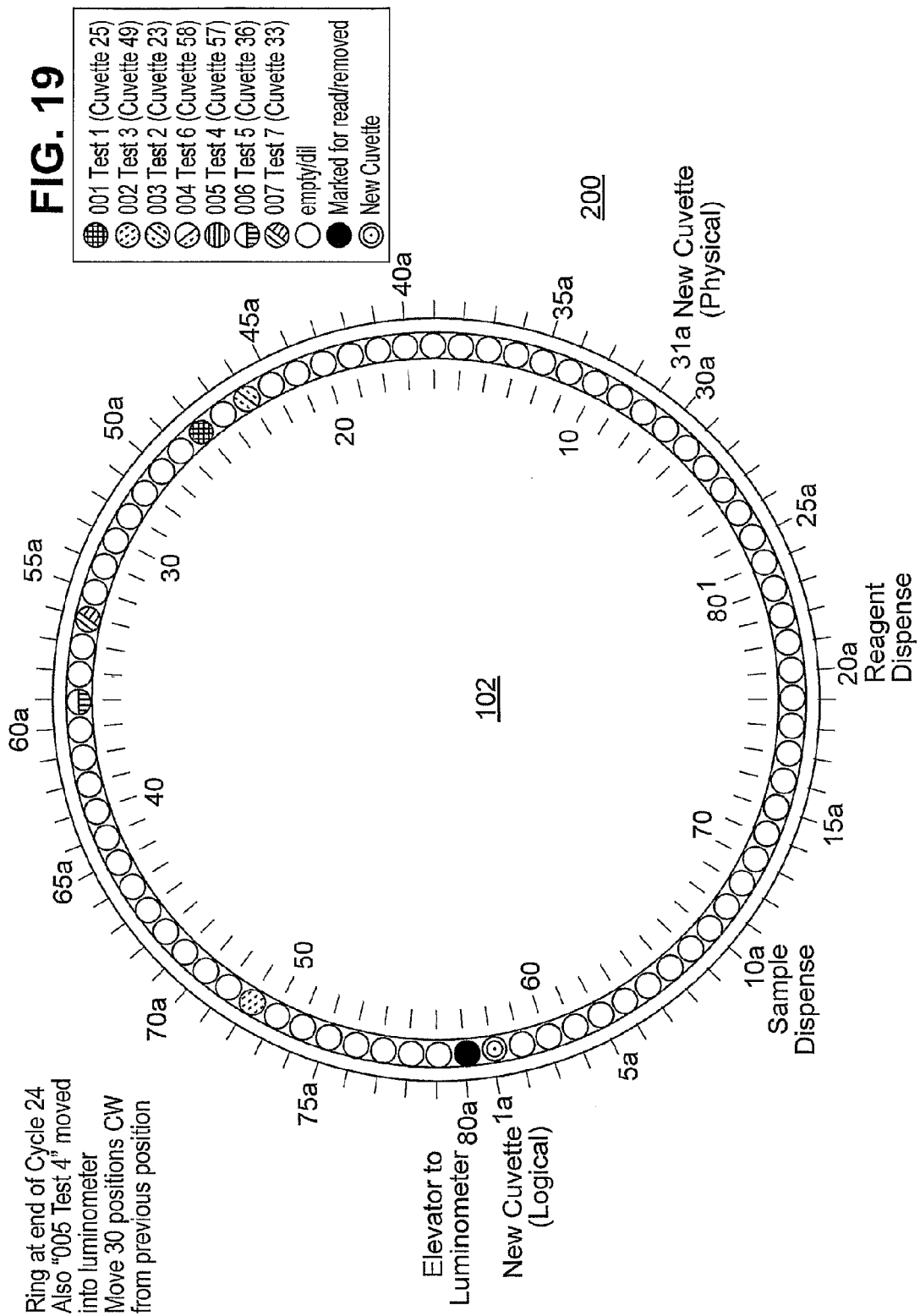

ASSAY TIMING IN A CLINICAL ANALYZER USING A CUVETTE CARRIER

BACKGROUND OF THE INVENTION

1. Field of the Invention

This invention relates to sample analysis systems for automated clinical analysis of biological fluid samples and more particularly to an apparatus and method that uses discrete reaction cuvettes and allows simultaneous performance of assays of varied predetermined incubation periods of samples and reagents. Preferably the cuvettes in the clinical analyzer traverse a closed path, such as a circular path of a cuvette ring.

2. Related Prior Art

In one known clinical analyzer, cuvettes for receiving sample and reagent are positioned one behind another in a straight line. The cuvettes are moved along a straight path or track, in a single direction, in movement cycles of fixed time duration. The movement cycles are often referred to as machine cycles or time cycles, (or just cycles, when clearly construed from the context), such as, for example, twenty seconds as used in a known clinical analyzer.

Each cuvette usually contains a discrete assay and each cuvette generally moves a fixed distance during each time cycle to a particular station to undergo a particular function, such as fluid delivery.

Fluid delivery is provided by separate fluid delivery stations that are usually located in a predetermined sequence alongside the straight track. As the cuvettes move progressively along their straight path of travel they pass each of the fluid delivery stations. Each cuvette receives a selected amount of sample, diluent, reagent, etc. from respective fluid delivery stations, depending upon the assay that is associated with each cuvette.

Another known clinical analyzer, as shown in European patent application 014064582, published Jan. 31, 1991, moves cuvettes along a circular path. The disclosed analyzer includes a circular reaction ring or cuvette ring that is rotatable about a central axis such that the cuvettes move along a circular path. Cuvette openings are spaced one next to another at a peripheral portion of the ring, which can accommodate, for example, 100 cuvettes. The cuvette ring rotates at fixed cyclic time intervals of, for example, 30 second duration.

Stations that perform fluid delivery or other functions, are usually provided near the periphery of the cuvette ring.

Whether a clinical analyzer moves cuvettes in a straight line path or along a circular path, or along any other non-linear path, of regular or irregular outline, the fluid delivery stations are usually provided at predetermined sequential locations along the travel path of the cuvette. Fluid delivery stations can also be combined with known robotically movable devices having selected ranges of movement. The collection of the events described in the succeeding paragraphs and the time durations and incubations between them is known as the assay protocol.

Each fluid delivery station may be specialized and set up to perform a specific fluid delivery function such as:

1. dispensation of sample into a cuvette;
2. dispensation of diluent into a cuvette;
3. dispensation of reagent into a cuvette;
4. dispensation of an ancillary material into a cuvette.

Probes that aspirate and dispense liquids such as reagent can also be washed and re-used before each aspiration/dispensation cycle. Probes that aspirate and dispense sample are sometimes removed and replaced before each aspiration/dispensation cycle.

Cuvettes in a clinical analyzer may also be subjected to the following functions:

1. transfer of a cuvette from its location in a track or cuvette ring to a luminometer;
2. light detection in a luminometer corresponding to a specific assay in a cuvette;
3. installation of a new cuvette in an open cuvette space in a track or cuvette ring if the cuvettes are not re-used;
4. washing of a cuvette after an assay is completed, if the cuvette is to be reused.

In order for a cuvette in a cuvette ring to receive fluid delivery or other function the cuvette ring rotates a predetermined amount during each time cycle, to move the cuvette step by step in each time cycle to a selected fluid delivery station or location. For example, the cuvette ring can rotate incrementally an amount equivalent to one cuvette space (the cycle distance) during each time cycle of movement.

Generally, the time it takes for a particular cuvette to reach a particular fluid delivery station or location is based on a predetermined incubation period of an earlier fluid delivery to the cuvette. The incubation time between sequential fluid deliveries is a multiple of the cycle duration and the number of time cycles it takes for a cuvette to move from one fluid delivery station to another fluid delivery station. The overall time period for an assay is the number of time cycles it takes for a cuvette to move from a first fluid delivery station to an assay read location where an assay reading can be made by a luminometer, for example.

Known clinical analyzers using a cuvette ring move the cuvettes in a predetermined fixed pattern every cycle, incrementing the ring position by a fixed number of positions every cycle to enable the introduction of a new test. This pattern may have multiple moves and stops to allow cuvettes to be positioned against the fluid delivery stations, wash station or read station, but the pattern repeats exactly every cycle. In one known clinical analyzer, the ring can have three different such patterns but within each such pattern the moves and stops are always the same.

It is well known that the physical layout of known clinical analyzers and the fluid delivery stations including the sequence and spacing of the fluid delivery stations and/or the location of robotically movable fluid delivery devices is generally based on a predetermined incubation period between consecutive fluid dispensations, such as sample dispensation and reagent dispensation.

Thus there is a tie between the incubation periods and the general physical layout of the fluid delivery systems in the known clinical analyzers. This tie severely limits or prevents the clinical analyzer from providing any variation in incubation time for different assays and as a result, the assay protocols are limited to having a few distinct values for the incubation durations.

I have found that I can break the tie between the physical layout of the fluid delivery system and assay timing by providing variable cuvette carrier motions in a fixed time cycle rather than be limited by non-variable movement of cuvettes along a circular path. Insofar as I am aware non-variable movement of cuvettes for a particular time cycle is prevalent in all known clinical analyzers that use a cuvette carrier.

I have discovered that by moving a cuvette in a cuvette ring from an initial selected reference location variable distances in selected directions to other selected locations for fluid delivery without waiting for fixed incremental ring movements in one direction, I can provide different incubation times between assay events that vary continuously, in multiples of the time cycle, within a wide range. This, in turn, provides the assay developers with much greater latitude in choosing the optimal incubation periods for each assay. Once the optimal incubation time periods are determined, the scheduling algorithms described in succeeding paragraphs will allow multiple assays of varying assay protocols to run in random-access.

By implementing variable movement of cuvettes in selected directions in a given time cycle I can also reduce the number of normally required fluid delivery stations from, for example, five to two. I can obtain this reduction in fluid delivery stations by moving different cuvettes, different distances at different incubation time intervals to two different fluid delivery stations (variable movement) for example, rather than have all cuvettes move at the same incubation time intervals in the same direction to each of five selected consecutive fluid delivery stations, for example.

In addition, I have found that with variable movement of cuvettes along a circular path in selected directions I can use priorities other than sequentially located fluid delivery stations to determine the physical layout of a clinical analyzer. For example I can conveniently locate fluid delivery stations based on conveniently available space and based on the ease of permitting access to the various fluid delivery and function stations in the clinical analyzer. In addition I can provide versatility in a fluid delivery station by enabling the same fluid delivery station to deliver one or more reagents and ancillary materials to a cuvette.

DESCRIPTION OF THE DRAWINGS

In the accompanying drawings,

FIG. 3 is a simplified schematic plan view of the cover tray for the cuvette ring;

FIGS. 5-19 are simplified schematic drawings of the movable cuvette ring relative to a fixed work surface at selected time cycles to show the activities being performed as indicated in the Table 3—Cycle Event Table.

Corresponding reference characters indicate corresponding parts throughout the several views of the drawings.

DETAILED DESCRIPTION OF THE INVENTION

Figure 1:
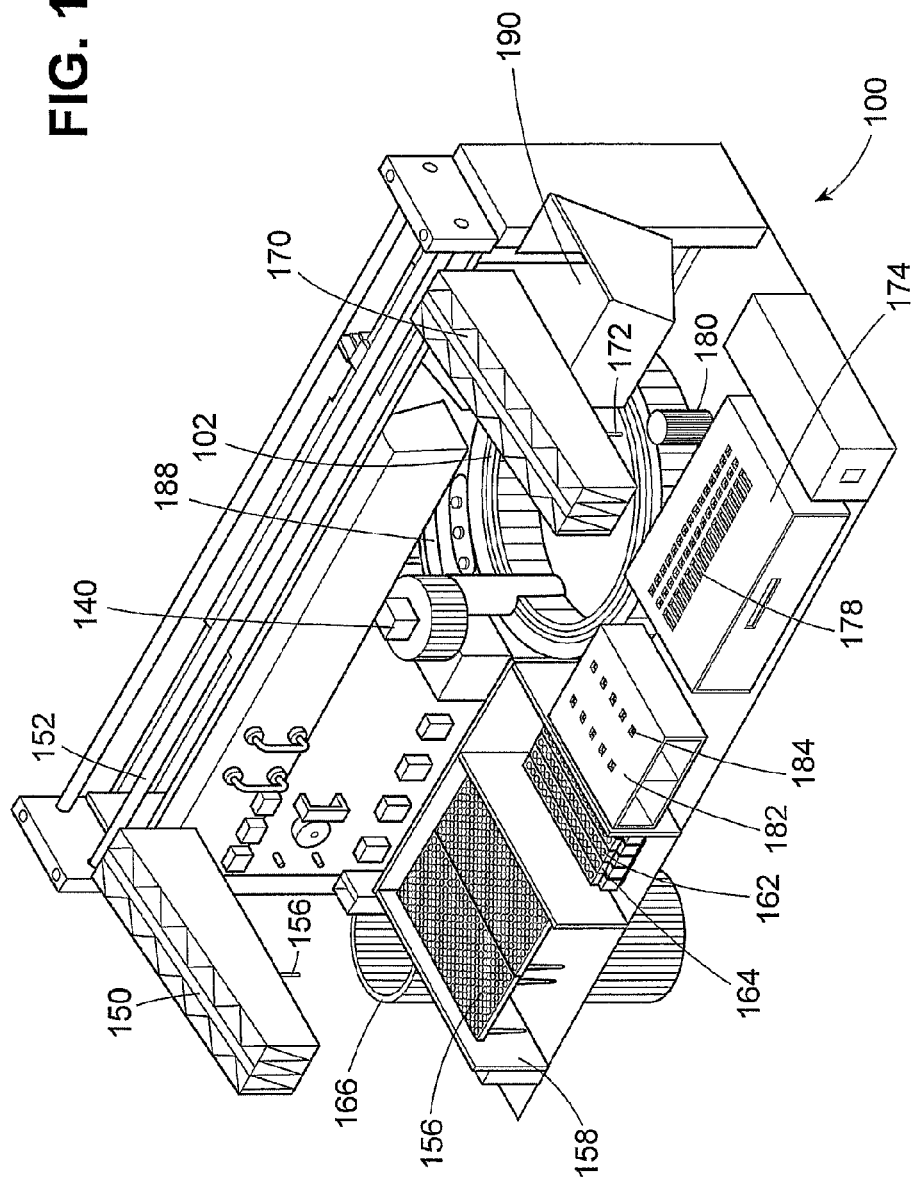
FIG. 1 is a simplified schematic drawing of a clinical analyzer incorporating the present invention.

A clinical analyzer incorporating one embodiment of the invention is generally indicated by the reference number 100 in FIG. 1.

Figure 2:
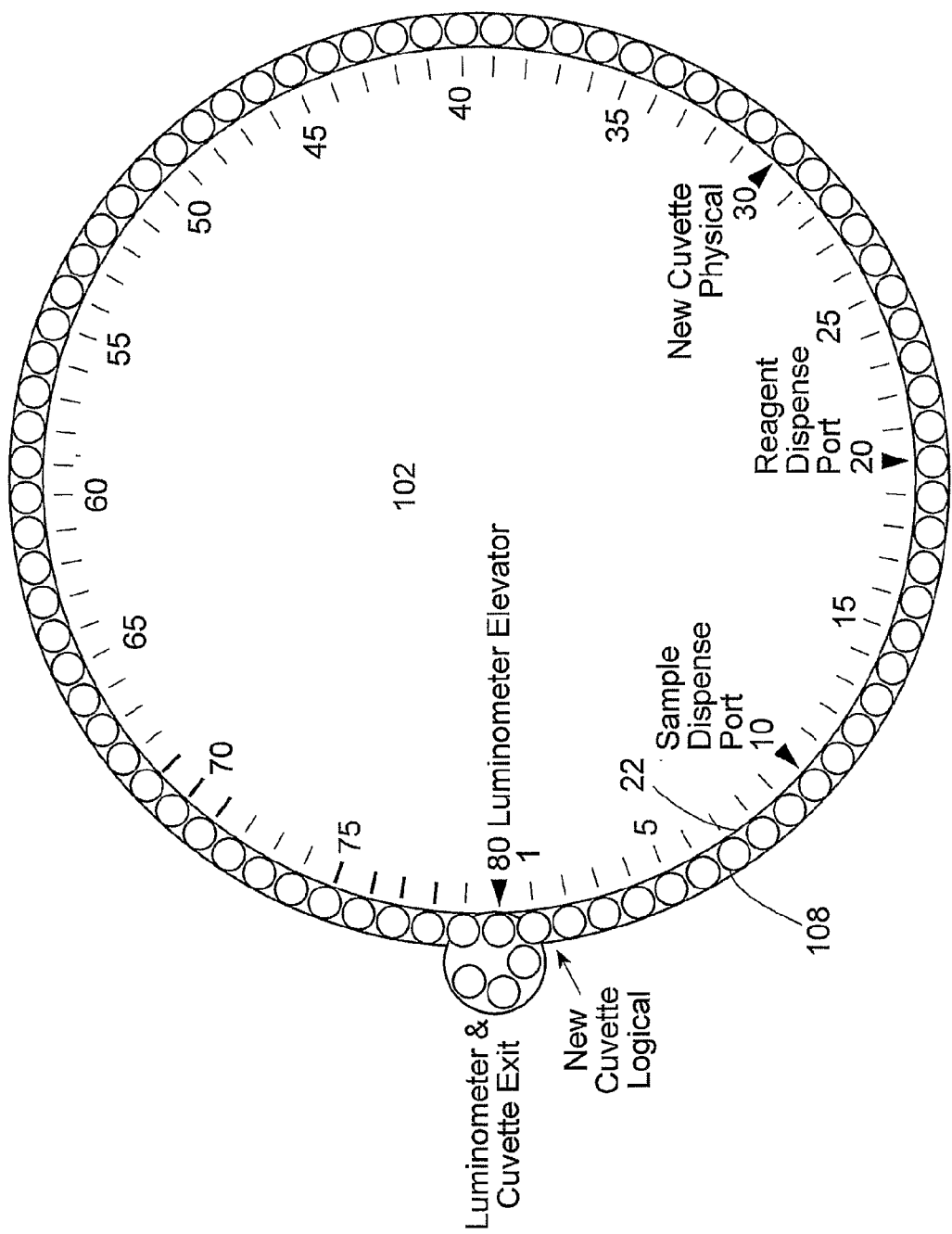
FIG. 2 is a simplified schematic plan view of the cuvette ring thereof.

The clinical analyzer 100 includes a cuvette ring or reaction ring 102 of known construction shown in simplified schematic form in FIG. 2. The cuvette ring 102 is movable in a horizontal plane about a central vertical axis. Movement of the cuvette ring 102 can be activated in a known manner by a suitable known stepping motor (not shown) with a known drive wheel (not shown) pressed against the outer circumference of the cuvette ring 102.

The cuvette ring 102 (FIG. 2) includes eighty cuvette openings, spaces, or positions equally spaced one next to another around a peripheral portion of the ring, with each cuvette opening accommodating a removable and preferably disposable cuvette 108, shown in simplified form as a circle.

Equally spaced indicia lines with numbers at intervals of 1, 5, 10, 15, 20, 25, 30, 35, 40, 45, 50, 55, 60, 65, 70, 75 and 80 along an inner border 22 of the movable cuvette ring 12 are intended to identify each of the eighty cuvettes and their corresponding cuvette spaces in the movable cuvette ring 102. Thus each number or indicia line on the cuvette ring corresponds to a distinct cuvette number or cuvette position and will be referred to by a number 1-80.

Figure 5:
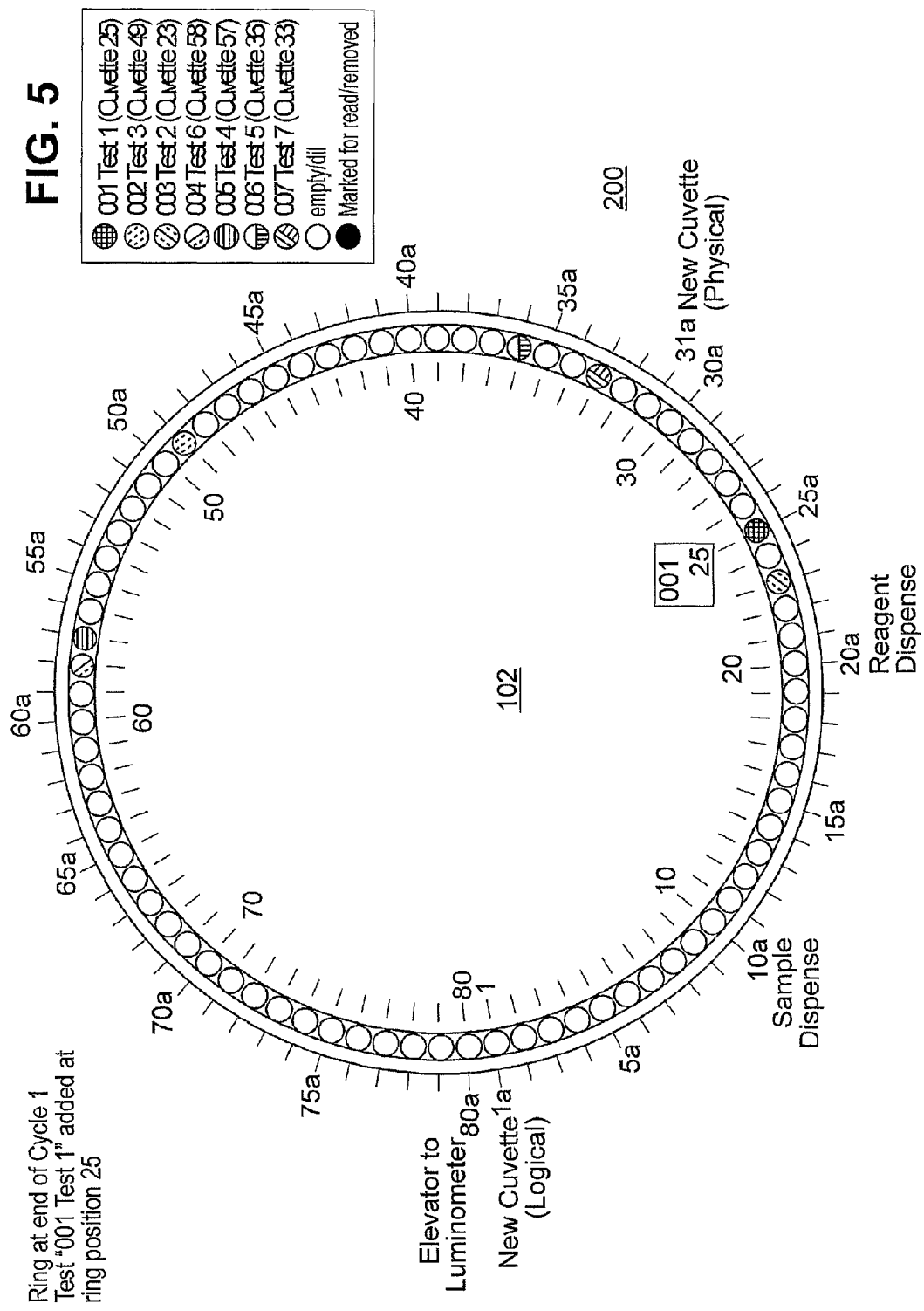

The cuvette ring 102 is bordered by a surrounding fixed surface 200 of the clinical analyzer 100 (FIG. 5).

For purposes of facilitating the description of this invention equally spaced cuvette reference indicia lines with numbers at intervals of 1a, 5a, 10a, 15a, 20a, 25a, 30a, 35a, 40a, 45a, 50a, 55a, 60a, 65a, 70a, 75a, and 80a are provided on the fixed surface 200 (FIG. 5) to correspond with and register with the indicia lines and numbers 1, 5, 10, 15, 20, 25, 30, 35, 40, 45, 50, 55, 60, 65, 70, 75 and 80 that represent the cuvette openings and cuvettes on the cuvette ring 102. All cuvette reference numbers and indicia lines on the fixed surface 200 indicate a distinct reference position and will be referred to in the description by a number 1-80 followed by the letter "a".

Although the cuvette ring 102 has eighty cuvette openings for eighty cuvettes, the number of cuvette openings in the ring 102 is a matter of choice.

The cuvette ring 102 has a suitable cover tray 110 (FIG. 3) which serves to protect the cuvettes 108 in the cuvette ring 102 from spillage or any other material that might otherwise fall into the cuvettes.

The cover tray 110 (FIG. 3), which does not rotate with the underlying cuvette ring 102 (FIG. 2), has two spaced port openings 114 and 116. Sample is dispensed through the port opening 114 into selected cuvettes in the cuvette ring 102, and reagent is dispensed through the port opening 116 into selected cuvettes in the cuvette ring 102. Although not shown, when the cover tray 110 is placed over the cuvette ring 102 of FIG. 5, the port opening 114 aligns with the cuvette reference position 10a on the fixed surface 200, and the port opening 116 aligns with the cuvette reference position 20a on the fixed surface 200.

Thus sample is dispensed at only one location on the cover tray 110, namely at the port opening 114, and reagent is dispensed at only one location on the cover tray 110, namely at the port opening 116. By limiting the port openings in the cover tray 110 through which sample and reagent are dispensed, evaporation of sample and reagent is minimized and contamination of cuvette ingredients is minimized.

The cover tray 110 (FIG. 3) also includes a port opening 120 through which new cuvettes are deposited into vacant cuvette spaces in the cuvette ring 102. The port opening 120 is the only opening in the cover tray 110 through which new cuvettes can be deposited into vacant cuvette spaces. Although not shown, when the cover tray 110 is placed over the cuvette ring 102 of FIG. 5, the port opening 120 aligns with the cuvette reference position 31a (FIG. 5) on the fixed surface 200.

The cover tray 110 (FIG. 3) further includes port openings 124, 126, 128, 130, 132, 134, 136 and 138. The port openings 124, 126, and 130 are for aspiration and dispense probes (not shown) used for a known wash operation, e.g. for immunoassays that use a solid phase capture such as magnetic particles. The port opening 132 is for an aspiration probe used in the wash operation. The port opening 128 is a wash dispense port and the port opening 134 is an acid injection port. The port 136 is a re-suspension port. The port 138 is a cuvette ejection port, wherein cuvettes pass upwardly through the cover tray 110 from the cuvette ring 102 for entry into a luminometer 140 in a known manner.

Although not shown, when the cover tray 110 is placed over the cuvette ring 102 of FIG. 5, the aspiration (wash) port opening 124 aligns with the cuvette reference position 69a, the re-suspension port opening 126 aligns with the cuvette reference position 70a, the wash dispense port opening 128 aligns with the cuvette reference position 71a, the wash dispense port opening 130 aligns with cuvette reference position 75a, the aspiration (wash) port opening 132 aligns with the cuvette reference position 76a, the acid injection port opening 134 aligns with the cuvette reference position 77a, the re-suspension port opening 136 aligns with the cuvette reference position 78a, and the cuvette ejection port opening 138 aligns with the cuvette reference position 80a.

Thus the reference positions 69a to 78a correspond to a wash station 188 (FIG. 1) for performing a known wash operation.

The analyzer 100 (FIG. 1) includes a sample pipettor robot 150 of known construction supported on an overhead rail 152 for movement along a horizontal plane and also in vertical directions. The sample pipettor robot 150 includes a disposable sample pipette or probe tip 156 that can descend and elevate relative to the sample dispense port opening 114 in the cover tray 110. The sample pipettor robot 150 is movable on the rail 152 over a bin 158 that stores probe tips 156. The sample pipettor robot 150 can access a selected disposable probe tip 156 in the bin 158 after a previously used probe tip 156 is detached from the sample pipettor robot 150. The sample pipettor robot 150 then elevates with the new probe tip 156 and moves over a sample rack tray 162 to enable the probe tip 156 to access a selected sample tube 164 in the sample rack tray 162. The sample pipettor robot 150 aspirates a predetermined amount of sample through the probe tip 156 from the selected sample tube 164 (FIG. 1).

The sample pipettor robot 150, with aspirated sample, descends to the sample dispense, port opening 114 in the cover tray 110 (FIG. 3) to dispense sample through the probe tip 156 and the sample dispense port opening 114 to a selected underlying cuvette 108, moved by the cuvette ring 102 (FIG. 2) into alignment with the sample dispense port opening 114 in the cover tray 110. After sample is dispensed into the selected cuvette 108, the sample pipettor robot 150 moves over a tip disposal container 166 (FIG. 1) for release of the disposable probe tip 156. All movements of the sample pipettor robot 150 are carried out in a known manner.

The analyzer 100 also includes a reagent pipettor robot 170 (FIG. 1) of known construction supported on the overhead rail 152 with the sample pipettor robot 150 or supported on a separate rail (not shown) spaced and parallel to the overhead rail 152. The reagent pipettor robot 170 also moves back and forth, and forward and backward, as does the sample pipettor robot 150, and includes a reagent pipette 172 that can descend and elevate relative to the reagent dispense port opening 116 in the cover tray 110 (FIG. 3).

The reagent pipette 172 is preferably non-disposable and reusable. The reagent pipettor robot 170 is movable over a reagent tray 174 (FIG. 1) to enable the reagent pipette 172 to enter a reagent access port 178 (FIG. 1) of a selected reagent container (not shown) held within the reagent tray 174. The reagent pipettor robot 170 aspirates a predetermined amount of reagent through the reagent pipette 172 from the reagent access port 178 and then moves to the reagent dispense port opening 116 (FIG. 3) in the cover tray 110. The reagent pipettor robot 170 then dispenses reagent through the reagent pipette 172 (FIG. 1) and the reagent dispense port opening 116 (FIG. 3) to a selected underlying cuvette 108 (FIG. 5) that has been moved by the cuvette ring 102 into alignment with the reagent dispense port opening 116 in the cover tray 110 (FIG. 3).

Once the reagent dispensation is completed, the reagent pipettor robot 170 is moved over a pipette wash station 180 (FIG. 1) of known construction to enable the non-disposable reagent pipette 172 (FIG. 1) to be washed in preparation for another reagent dispensing function.

The reagent pipettor robot 170 can also be used for dispensing ancillary material, e.g. a common reagent such as sample pretreatment material or diluent, from an ancillary tray 182 (FIG. 1) after the reagent pipette 172 is washed. Thus, the reagent pipettor robot 170 can be positioned over the ancillary tray 182 for descent to an ancillary material access port 184 (FIG. 1). The reagent pipettor robot 170 aspirates a predetermined amount of ancillary material from the access port 184 and then moves over to the reagent dispense port opening 116 (FIG. 3) in the cover tray 110.

The reagent pipettor robot 170 dispenses a selected amount of ancillary material through the reagent pipette 172 and the reagent dispense port opening 116 into a selected underlying cuvette 108 (FIG. 2) that has been moved by the cuvette ring 102 into alignment with the reagent dispense port opening 116 (FIG. 3) in the cover tray 110. After reagent dispensation is completed, the non-disposable reagent pipette 172 is moved over the wash station 180 (FIG. 1) for washing of the reagent pipette 172 in preparation for another aspiration and dispensation function of the reagent pipettor robot 170. All movements of the reagent pipettor robot 170 are carried out in a known manner.

The clinical analyzer 100 further includes the luminometer 140 (FIG. 1) of known construction for light detection of reactions in cuvettes 108 (FIG. 2) that have completed their earlier assay operations including incubation with sample, reagent, ancillary material and wash functions. The luminometer 140 is located near the cuvette space 80 of the cuvette ring 102 of FIG. 2. Cuvettes 108 that are undergoing a light emitting reaction suitable for detection in the luminometer 140 provide analytical data that is used in the analysis or assay of different blood characteristics that are tested in each cuvette that receives sample and reagent.

At the appropriate time that a cuvette 108 (FIG. 5) in the cuvette ring 102 is ready for assay reading in the luminometer 140 (FIG. 1) the assay readable cuvette 108 will be in alignment with a known cuvette ejector or elevation device (not shown). The cuvette ejector device (not shown) pushes or otherwise transfers the assay readable cuvette 108 upwardly from the cuvette ring 102 into the luminometer 140. A vacant cuvette opening is thus left in the cuvette ring 102. The assay readable cuvette 108 that is received in the luminometer 140 remains inside the luminometer until the light detection or read operation is completed. In the clinical analyzer 100 the read operation includes dispensing a base material, generation of a light flash, reading the light emitted, and evacuation of the cuvette contents (not shown). After the read operation is completed, the cuvette 108 is ejected (not shown) from the luminometer 140 into a suitable disposal container (not shown).

The clinical analyzer 100 also includes a known wash station 188 (FIG. 1) next to the luminometer 140. The wash station 188 aligns the port openings 124-136 in the cover tray 110 (FIG. 3) and prepares cuvettes, in a known manner, for entry into the luminometer 140. Thus as cuvettes 108 (FIG. 2) in the cuvette ring 102 move past the wash station 188 (FIG. 1) they are operated on in a known manner by the wash station 188 to ensure that the reacting components in the cuvettes 108 emit the quantities and qualities of light that permit the luminometer 140 to adequately read the resulting light emissions and thus provide the data needed for each assay.

A cuvette loader 190 (FIG. 1) of known construction deposits a new cuvette 108 into the vacant cuvette opening in the cuvette ring 102 (FIG. 2) to replace a previously removed cuvette 108. The cuvette loader 190 can also load the cuvette spaces of the cuvette ring 102 with cuvettes 108 for each new start-up operation of the clinical analyzer 100.

In accordance with the present invention, the cuvette ring 102 has a preferred movement time cycle duration, such as twenty seconds. The movement time cycle duration is a matter of choice. A schematic illustration of the possible known functions that can be scheduled to occur during the twenty second time cycle is shown in the Timing Table of FIG. 4.

Figure 4:
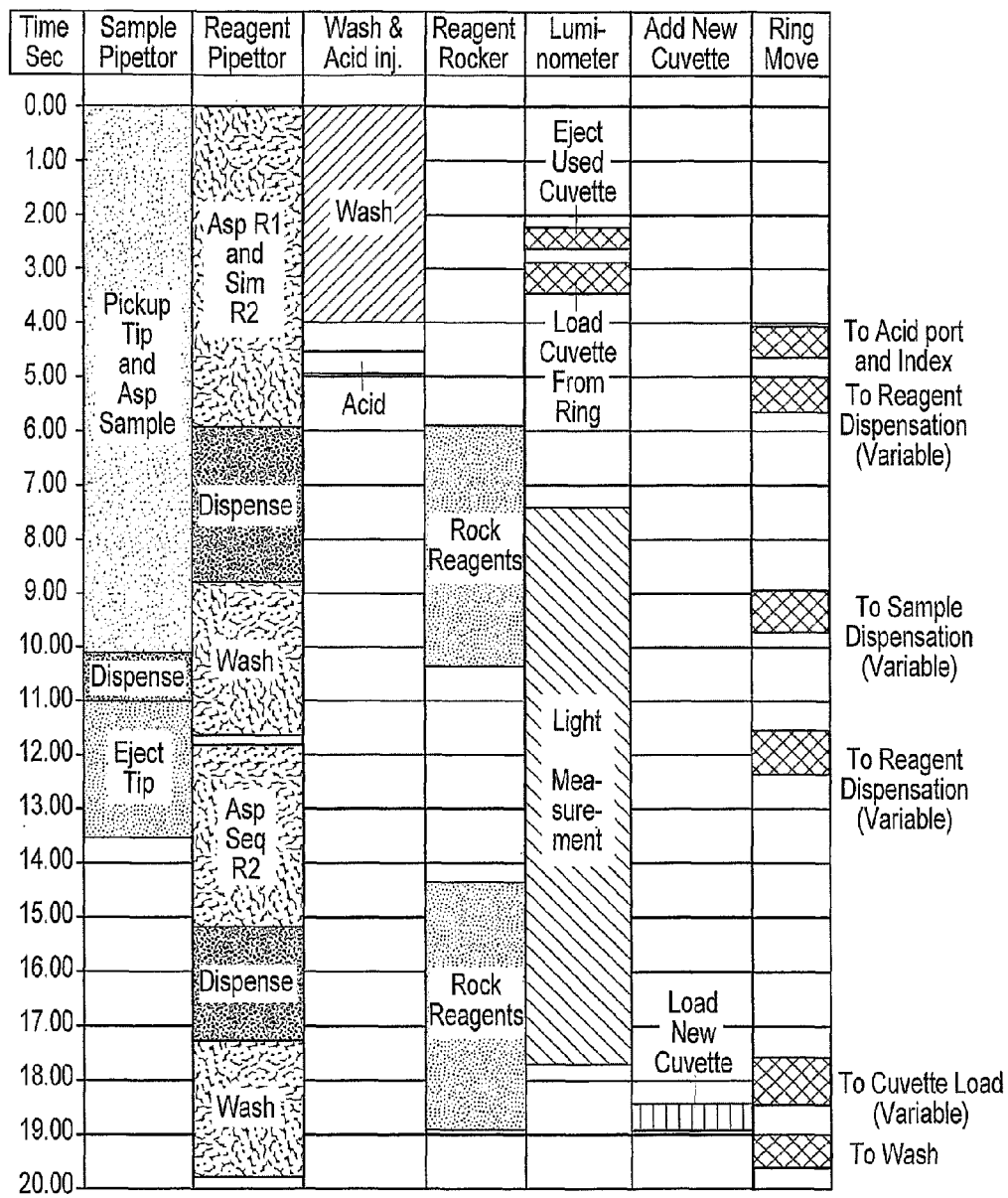
FIG. 4 is a simplified timing table for the clinical analyzer, detailing the events that occur in every time cycle.

Referring to the Timing Table of FIG. 4, each individual second of the 20 second time cycle is indicated in the first column entitled Time/Second.

The second column in the Timing Table of FIG. 4, entitled Sample Pipettor indicates the specific time allocations within the twenty second time cycle for performance of various functions by the sample pipettor robot 150 (FIG. 1). Thus the sample pipettor robot 150 operates in the first 10 seconds of the 20 second time cycle to pick up a pipette tip 156 (FIG. 1) and aspirate sample in a known manner from a selected sample container in the sample tray 162.

As further indicated in the Sample Pipettor column of FIG. 4, between the $10^{th}$ the $11^{th}$ second of the 20 second time cycle, the sample pipettor robot 150 dispenses aspirated sample, and between the $11^{th}$ and the 13.5 second segment of the second time cycle the sample pipettor robot 150 ejects the sample pipette tip 156. The sample pipettor robot 150 has no scheduled activity after 13.5 seconds of the 20 second time cycle.

The third column of the Timing Table of FIG. 4 entitled Reagent Pipettor indicates the specific time allocations within the twenty second time cycle for performance of various functions by the reagent pipettor robot 170 (FIG. 1). Thus the reagent pipettor robot 170 operates in the first six seconds of the 20 second time cycle to aspirate a first reagent R1 from the reagent tray 174 (FIG. 1) followed immediately by aspiration of a second reagent R2 if needed. Both reagents R1 and R2 are simultaneously dispensed. However, if there is no need for consecutive aspiration of a second reagent R2, then the dispense operation will be limited to the reagent R1.

Thus between the $6^{th}$ and $9^{th}$ second of the 20 second time cycle the reagent pipettor robot 170 can simultaneously dispense whatever reagent R1 (and possibly R2) that was aspirated during the first six seconds of the time cycle. Between slightly less than nine seconds and slightly more than 11 seconds of the 20 second time cycle the reagent pipette 172 is washed at the wash station 180 (FIG. 1) before the reagent pipettor robot 170 can begin another aspiration cycle.

As further indicated in the Reagent Pipettor column of FIG. 4, between the time period of slightly less than 12 seconds to slightly more than 15 seconds of the second time cycle the reagent pipettor robot 170 can aspirate another second reagent R2 if needed. Between slightly more than 15 seconds to slightly more than 17 seconds of the 20 second time cycle the reagent pipettor robot 170 can dispense the additional second reagent R2. The reagent pipette 172 is washed at the wash station 180 (FIG. 1) in the time segment between slightly more than 17 seconds until slightly less than 20 seconds.

The fourth column of the Timing Table of FIG. 4 entitled Wash and Acid Injection indicates the specific time within the 20 second time cycle that is allocated to the washing of cuvettes at the wash station 188 (FIG. 1) before the assay readable cuvettes 108 (FIG. 2) are ejected from the cuvette ring 102 into the luminometer 140 (FIG. 1). An acid ingredient is also dispensed at the wash station 188 between the fourth and fifth seconds of the 20 second time cycle (FIG. 4). The wash and acid injection are known operations.

The fifth column of the Timing Table of FIG. 4 entitled Reagent Rocker indicates the specific time allocated to the rocking or mixing of reagent containers. The reagent rocking occurs twice in the 20 second time cycle. The first rocking operation extends from less than 6 seconds of the 20 second time cycle to slightly more than 10 seconds. The second rocking operation extends from slightly more than 14 seconds to slightly less than 19 seconds. The rocking of reagents is a known operation to ensure even distribution of the ingredients in the reagent tray 174 (FIG. 1).

The sixth column of the Timing Table of FIG. 4 entitled Luminometer indicates the specific time periods allocated to the operations associated with the luminometer 140 (FIG. 1). For example, for a fraction of a second between the $2^{nd}$ and $3^{rd}$ second of the 20 second time cycle, a cuvette 108 (FIG. 2) that has completed the read operation in the luminometer 140 is ejected from the luminometer. In another fraction of a second between the time interval of slightly less than 3 seconds to slightly more than 3 seconds, an assay cuvette 108 on the cuvette ring 102 (FIG. 2) that is ready for a light detection or read operation is elevated or ejected from the cuvette ring 102 into the luminometer 140 (FIG. 1). Light measurement or light detection within the luminometer 140 that constitutes the read operation, occurs during the time period of slightly more than 7 seconds to slightly less than 18 seconds of the 20 second time cycle.

The seventh column of the Timing Table of FIG. 4 entitled Add New Cuvette indicates that the new cuvette loading procedure occurs between the $18^{th}$ and $19^{th}$ seconds of the 20 second time cycle.

Figure 2B:
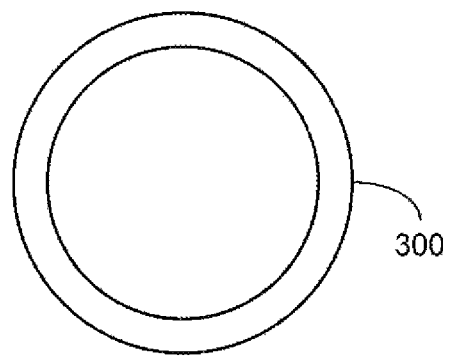
FIG. 2B is a simplified schematic plan view of a magnetic ring.

The eighth column of the Timing Table of FIG. 4 entitled Ring Movement indicates by blank spaces, the portions of the 20 second time cycle when the cuvette ring 102 (FIG. 2) is stationary. The stationary periods align with actions on the cuvettes, such as sample and reagent dispensation, cuvette ejection and installation, and wash operations, as indicated in the other columns of FIG. 4 The cuvette ring 102 is stationary during the first 4 seconds of the time cycle to allow the performance of a wash operation. From the $4^{th}$ second to slightly less than the $5^{th}$ second, movement of the cuvette ring 102 permits relative indexing between a known magnetic ring segment 300 (FIG. 2B, 2C, 2D) and the cuvette ring 102, in a known manner.

Figure 2C:
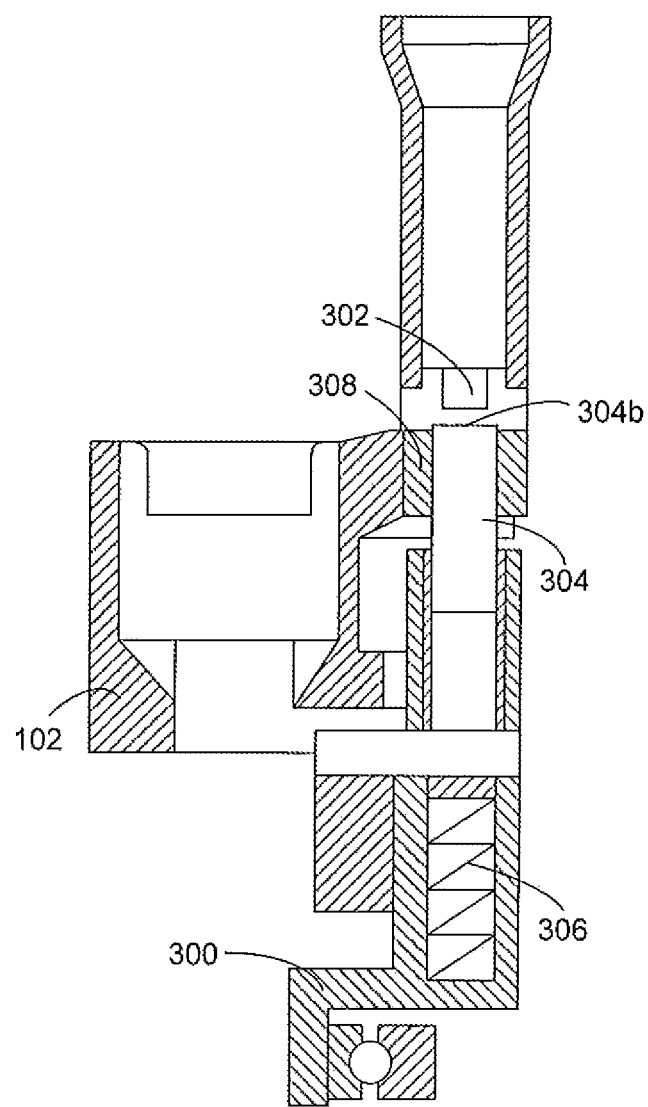
FIG. 2C is a simplified schematic side-view of the cuvette ring engaged to a portion of the magnetic ring.
Figure 2D:
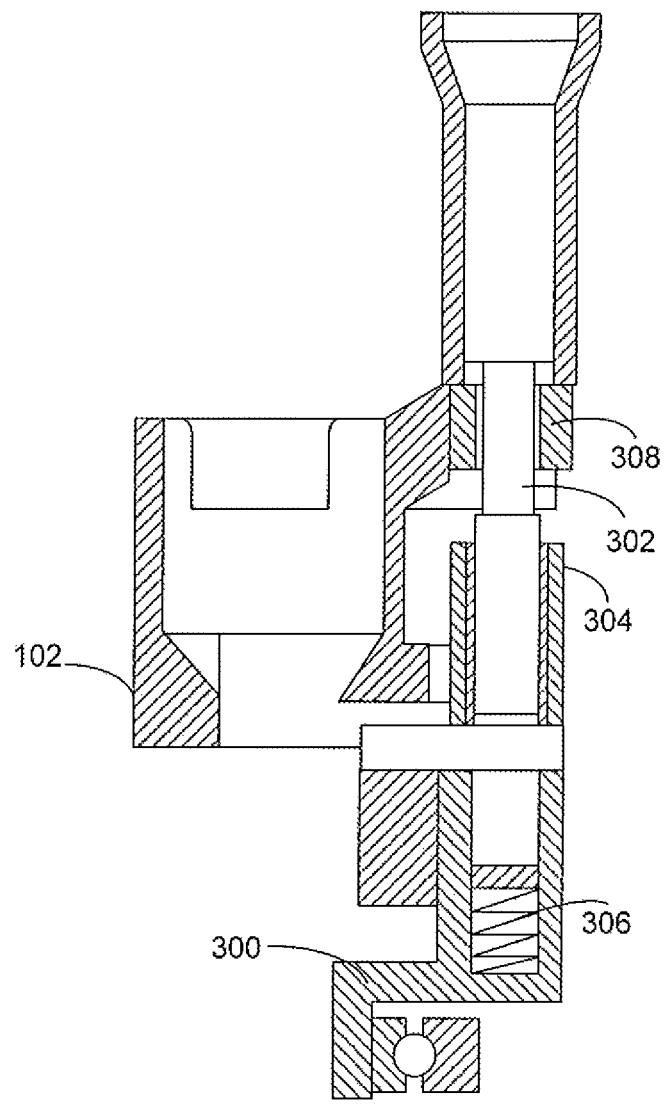
FIG. 2D is a simplified schematic side-view of the cuvette ring disengaged from a portion of the magnetic ring.

The magnetic ring segment 300 normally moves with the cuvette ring 102 (FIG. 2C) for slightly more than 19 seconds of the 20 second time cycle. Similar to the magnetic ring mechanism described in FIGS. 6 and 6A of U.S. Pat. No. 5,827,478, the mechanism includes a plunger 302, and when the plunger 302 is in its up position, a detent pin 304 coupled to the magnet ring 300, is placed in its detent position. When the detent pin 304 is in its detent position a detent spring 306 forces an end 304b of the detent pin 304 through a slot formed in a wall region 308 of the cuvette ring 102 as shown in FIG. 2C. Thus, in the detent position, the detent pin 304 engages the cuvette ring 102 and locks or couples, the cuvette ring 102 to the magnet ring 300 thereby allowing the cuvette ring 102 to move with the magnet ring 300, instead of allowing the cuvette ring 102 to move relative to the magnet ring 300. During the period that begins after 4 seconds and ends at approximately 4.5 seconds (FIG. 4) the magnetic ring segment 300 detaches from the cuvette ring 102 (FIG. 2D) to enable the magnetic ring 300 to index one cuvette space with respect to the cuvette ring 102. For example, and as described in U.S. Pat. No. 5,827,478, and as shown in FIG. 2D, the plunger 302 drives the detent pin 304 against the detent spring 306 until the detent pin 304 is pushed completely through the slot in the wall region 308 of the cuvette ring 102. At this point, the cuvette ring 102 is de-coupled from the magnet ring 300 and can therefore move relative to the magnet ring 300. After the indexing operation, the magnet ring 300 again engages with the cuvette ring 102 (FIG. 2C) for movement with the cuvette ring 102. This operation of magnetic ring 300 engagement/disengagement from the cuvette ring 102 is a known operation and the mechanism for enabling this magnetic ring detachment and re-engagement with the cuvette ring is a known mechanism. For example, U.S. Pat. No. 5,827,478, describes a cuvette ring movably coupled to a magnetic ring, where the magnetic ring and cuvette ring have circular shapes.

As further indicated in the Ring Movement column of the Timing Table of FIG. 4, the cuvette ring 102 (FIG. 2) is stationary for a fraction of a second between the $4^{th}$ and $5^{th}$ seconds for acid dispense. The cuvette ring 102 then moves from approximately the $5^{th}$ second to slightly less than the $6^{th}$ second to bring a cuvette to a reagent dispensation position. The cuvette ring 102 then stops from the 5.5 second point to slightly less than 9 seconds to enable reagent dispensation. The cuvette ring 102 then moves for slightly less than 1 second to bring a cuvette to a sample dispensation location.

Sample is dispensed from slightly less than 10 seconds up to approximately 11.5 seconds. The cuvette ring 102 then moves from approximately the 11.5 second point to slightly more than the $12^{th}$ second to bring another cuvette to the reagent dispensation location. The cuvette ring 102 is stationary from slightly more than the $12^{th}$ second up to approximately 17.5 seconds for the second reagent dispensation. The cuvette ring 102 then moves for approximately 1 second to bring a cuvette to the cuvette loading position (if needed). The cuvette ring 102 stops for a fraction of a second between the $18^{th}$ and $19^{th}$ seconds to load a new cuvette in an open space on the carrier when it again moves for approximately half a second to bring a cuvette to the wash station.

All of the processes and operations indicated in the Timing Table of FIG. 4 are known processes. However I have recognized that variable movement of the cuvette ring 102 during a fixed time cycle can permit attainment of varying predetermined incubation periods which is a fundamental feature of this invention. The timing and scheduling of such processes or operations to permit variable movement of the cuvette ring 102 during a fixed time cycle is also a fundamental feature of this invention.

Thus, variable rotational movement of the cuvette ring 102 during the fixed time cycle enables any assay being performed in a particular cuvette to be processed simultaneously along with other assays being performed in other cuvettes, all running with different incubation periods or different assay protocols.

Selecting the assay to be performed in each cuvette 108 (FIG. 2) of the cuvette ring 102 is obtainable by scheduling the predetermined incubation period for each fluid dispensation in each cuvette, and controlling cuvette ring movement during each time cycle to permit timely fluid dispensations without conflicting with any of the other fluid dispensations, or any other operation of the clinical analyzer.

Thus, one of the keys to achieving predetermined incubation periods for each different assay is the scheduling of such assays such that no conflicts occur. Another key to achieving predetermined incubation periods for each cuvette is the programming of variable cuvette ring movement to coordinate with the operation of the various fluid dispensing mechanisms and other functional devices that provide a contribution to the clinical analysis of samples.

To illustrate the operation of the clinical analyzer with variable cuvette carrier movement, a series of simplified tests will be described including the manner of coordinating such tests so that they can be carried out without conflict.

Samples that are to be tested in the clinical analyzer are generally brought to an operator in random order without regard to the particular parameter that is being tested. For example, a sample may be subjected to one or more tests, and each test is carried out in an individual cuvette. A series of tests on a sample is known as a panel, such as a thyroid panel, an anemia panel or a routine physical examination blood panel. Each individual test or assay whether or not it is part of a panel of tests is carried out in an individual cuvette.

For example, the following Worklist of Table 1 has an agenda of seven tests to be performed.

TABLE 1

| Worklist | |
|---|---|
| Sequence of Arrival | Test Number |
| 1 | Test 1 |
| 2 | Test 2 |
| 3 | Test 3 |
| 4 | Test 6 |
| 5 | Test 4 |
| 6 | Test 5 |
| 7 | Test 7 |

The Table 1 Worklist agenda is compiled as each test order or test request is given or otherwise communicated to an operator of the clinical analyzer. The Sequence of Arrival column in the Table 1 Worklist indicates the sequential order of arrival of the tests at the clinical analyzer. The Test Number column in the Worklist Table 1 indicates the type of test that is being performed.

Letters, numbers or a combination of letters and numbers or any other suitable identification can be used to identify the type of test being performed. Thus Test 1 may be for Folate. Test 2 may be for Testosterone. Test 3 may be for B12. Test 4 may be part of a thyroid panel. Test 5 may be for digoxin. Test 6 may be for estradiol, and Test 7 may be a test for phenytoin.

For discussion purposes each of the test numbers 1-7 in the Table 1 Worklist will be the subject of a single test corresponding to a single cuvette.

The cuvette ring 102 (FIG. 2) starts each time cycle at a reference position known as an increment position. At the end of the first stationary period for the ring as indicated in the table in FIG. 4, the ring indexes one position counter-clockwise to a new increment position. Within the fixed 20 second time duration of each cycle the cuvette ring 102 may also move variable amounts away from the increment position to accomplish selected functions for selected cuvettes. If any other ring moves occur during the time cycle, they will be compensated for at the end of the cycle by a final move of the ring that will bring it back to the new increment position, also defined as the incremented position. Therefore, the increment position of a given time cycle is the incremented position of the previous time cycle. Thus, the increment position of the cuvette ring 102 changes each time cycle by advancing in a predetermined counter-clockwise direction by one cuvette in each time cycle.

Referring to FIG. 5, each of the 80 cuvettes or cuvette positions or spaces in the cuvette ring 102 are distinctly identified by a numbered position 1-80, for discussion purposes. The position of the cuvette ring 102 in FIG. 5 corresponds to the test conditions at the end of a soon to be described cycle 1 of the clinical analyzer 100.

The fixed surface 200 in FIG. 5 includes eighty numbered reference positions that remain fixed and register with the eighty movable cuvette spaces on the cuvette ring 102. The eighty numbered reference positions on the fixed surface 200, which are also provided for discussion purposes, serve as reference indicators to facilitate visualization of the changes in position of the eighty cuvettes on the cuvette ring 102 during movement of the cuvette ring 102.

The incremented conditions at the end of a first time cycle and before a second time cycle are indicated in FIG. 5, wherein the cuvette 25 in the cuvette ring 102 aligns with the fixed reference position 25a on the fixed surface 200. The cuvette 25 is the first cuvette, of seven sequential tests, to receive sample.

The movement pattern of the cuvette ring 102, following incremental movement, during any twenty second time cycle is entirely variable and can differ in each and every time cycle of movement of the clinical analyzer 100. However the cuvette ring 102 will always return to its newly incremented position at the end of each time cycle.

Figure 6:
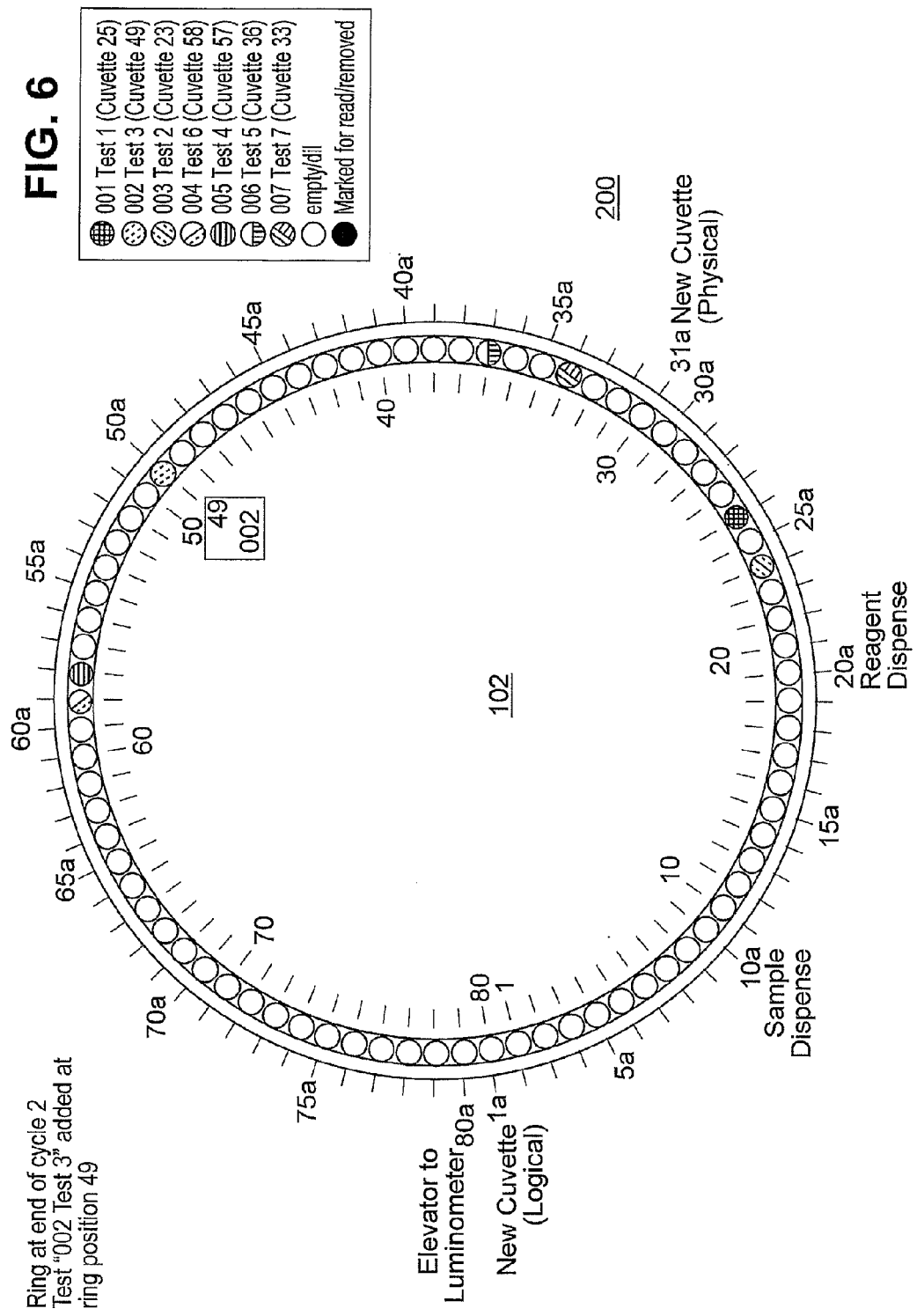

For example, between the beginning and end of a second time cycle as indicated in FIG. 6, the cuvette ring 102 is indexed one cuvette position or one reference position on the fixed surface 200 from the incremented ring position of FIG. 5. Thus in FIG. 6 the Test 1 cuvette (cuvette 25) of the cuvette ring 102 now aligns with the reference position 26a on the fixed surface 200 of the clinical analyzer 100.

In each succeeding time cycle the cuvette ring 102 will index one reference position per time cycle. Such indexing may be followed by variable rotational movements of the cuvette ring 102 in selected distances and selected directions for the purpose of dispensing sample and reagent and the performance of other functions of the clinical analyzer. However after all variable movements are completed, the cuvette ring 102, before the end of the fixed time cycle, will return to its incremented position.

Most assays in a clinical analyzer usually have three distinct incubation periods. One incubation period occurs in the time duration between sample dispensation and dispensation of a first reagent (R1). A second incubation period can occur between dispensation of a first reagent (R1) and dispensation of a second reagent (R2). A third incubation period can occur between dispensation of a second reagent (R2) and the read operation in the signal reading station, where, for example a luminometer is used as a signal reader. An overall incubation period is the total time of the first, second and third incubation periods between the dispensation of sample and the read operation.

Incubation times for each of the three incubation periods previously described are determined during assay development to achieve optimal clinical utility and are preprogrammed into the instrument.

In accordance with the invention, once an incubation time is determined, the incubation time is divided by the cuvette ring movement cycle time of 20 seconds to ascertain the number of time cycles of cuvette ring movement that must occur in correspondency with the incubation time. Thus the incubation time can be of any selected time duration that is a multiple in whole numbers of the time duration of the cuvette ring movement cycle time.

The following Table 2—Test Definition Timing Parameters (Tdef), indicates the predetermined timing parameters or incubation periods for each of the seven tests listed in the Table 1—Worklist.

TABLE 2

Test Definitions - Timing Parameters (Tdef)

| Test ID | Sample | R1 | R2 | Read | Overall |
|---------|--------|----|----|------|---------|
| Test 1  | 0      | 15 | 20 | 21   | 56      |
| Test 2  | 0      | 14 | 23 | 19   | 56      |
| Test 3  | 0      | 10 | 10 | 11   | 31      |
| Test 4  | 0      | 5  | 8  | 7    | 20      |
| Test 5  | 0      | 5  | 13 | 22   | 40      |
| Test 6  | 0      | 5  | 7  | 8    | 20      |
| Test 7  | 0      | 16 | 8  | 17   | 41      |

Dispensation of sample into a cuvette for each test in the Table 2—Test Definitions—Timing Parameters is considered to occur at the beginning of the incubation period for that sample or at "0" time.

Dispensation of reagent R1 into a cuvette for each of the seven tests in Table 2 occurs after a dispensed sample has incubated for the predetermined number of time cycles indicated in the column R1 of Table 2. Such incubation may be necessary for temperature equilibration or if the sample was delivered with pretreatment agent. Dispensation of the reagent R2 for each of the seven tests of Table 2 occurs after the sample and the reagent R1 have incubated for the predetermined number of time cycles indicated in the column R2 of Table 2.

The read operation for each of the seven tests of Table 2 occurs after the sample, the reagent R1, and the reagent R2 have incubated for the predetermined number of time cycles indicated in the Read column of Table 2. Thus the overall predetermined incubation time or total number of time cycles for a particular assay to be completed in the clinical analyzer, from sample dispensation to read operation is indicated in the Overall column of Table 2.

Table 2 does not necessarily indicate the order in which the seven listed tests are to occur. The order in which each of the seven tests occurs is determined by a cycle event analysis as indicated in the following simplified Table 3—Cycle Event Table.

TABLE 3

Cycle Event Table

| Time Cycle | Sample | R1 | R2 | Read | New Cuvette | Ring Position at Luminometer |
|---|---|---|---|---|---|---|
| 1 | 001 Test 1 | | | | | 80 |
| 2 | 002 Test 3 | | | | | 79 |
| 3 | 003 Test 2 | | | | | 78 |
| 4 | 004 Test 6 | | | | | 77 |
| 5 | 005 Test 4 | | | | | 76 |
| 6 | 006 Test 5 | | | | | 75 |
| 7 | (dilution) | Dil addition | | | | 74 |
| 8 | 007 Test 7 | | | | | 73 |
| 9 | | 004 Test 6 | | | | 72 |
| 10 | | 005 Test 4 | | | | 71 |
| 11 | | 006 Test 5 | | | | 70 |
| 12 | | 002 Test 3 | | | | 69 |
| 13 | | | | | | 68 |
| 14 | | | | | | 67 |
| 15 | | | | | | 66 |
| 16 | | 001 Test 1 | 004 Test 6 | | | 65 |
| 17 | | 003 Test 2 | | | | 64 |
| 18 | | | 005 Test 4 | | | 63 |
| 19 | | | | | | 62 |
| 20 | | | | | | 61 |
| 21 | | | | | | 60 |
| 22 | | | 002 Test 3 | | | 59 |
| 23 | | | | | | 58 |
| 24 | | 007 Test 7 | 006 Test 5 | 004 Test 6 | 004 Test 6 | 57 |
| 25 | | | | 005 Test 4 | 005 Test 4 | 56 |
| 26 | | | | | | 55 |
| 27 | | | | | | 54 |
| 28 | | | | | | 53 |
| 29 | | | | | | 52 |
| 30 | | | | | | 51 |
| 31 | | | | | | 50 |
| 32 | | | 007 Test 7 | | | 49 |
| 33 | | | | 002 Test 3 | 002 Test 3 | 48 |
| 34 | | | | | | 47 |
| 35 | | | | | | 46 |
| 36 | | | 001 Test 1 | | | 45 |
| 37 | | | | | | 44 |
| 38 | | | | | | 43 |
| 39 | | | | | | 42 |
| 40 | | | 003 Test 2 | | | 41 |
| 41 | | | | | | 40 |
| 42 | | | | | | 39 |
| 43 | | | | | | 3 |
| 44 | | | | | | 37 |
| 45 | | | | | | 36 |
| 46 | | | | 006 Test 5 | 006 Test 5 | 35 |
| 47 | | | | | | 34 |
| 48 | | | | | | 33 |
| 49 | | | | 007 Test 7 | 007 Test 7 | 32 |
| 50 | | | | | | 31 |
| 51 | | | | | | 30 |
| 52 | | | | | | 29 |
| 53 | | | | | | 28 |
| 54 | | | | | | 27 |
| 55 | | | | | | 26 |
| 56 | | | | | | 25 |
| 57 | | | | 001 Test 1 | 001 Test 1 | 24 |
| 58 | | | | | | 23 |
| 59 | | | | 003 Test 2 | 003 Test 2 | 22 |

The Table 3—Cycle Event Table schedules activities for each of the seven tests listed in the Table 2—Test Definitions—Timing Parameters, based on the timing parameters for each test that are indicated in Table 2.

The Table 3—Cycle Event Table schedules sample dispensation, reagent dispensation, read operation and other requisite operations such as sample dilution and cuvette replacement to ensure that no conflicts occur.

A conflict is defined as a scheduling of two operations to occur at the same time, but which, as a practical matter cannot occur at the same time because of time limitations indicated in the Timing Table of FIG. 4. Examples of conflicting operations are a scheduling of two sample dispensations at the same time, two reagent dispensations at the same time, two luminometer readings at the same time or two new cuvette installations at the same time. A program for producing the Table 3—Cycle Event Table or for scheduling the test activities such that no conflicts occur can be developed in any suitable known manner by persons having ordinary skill in the art.

The Table 3—Cycle Event Table is analogous to a reservation system for an airline, where seats that are initially available eventually become occupied. This seat availability and unavailability can be analogized to available time slots in the Table 3—Cycle Event Table. Because of variability and timing of the incubation periods for different tests, there is a possibility that a time slot in the Table 3—Cycle Event Table is already occupied. Therefore if a time slot for a particular test B is already occupied by an activity for another test A, then the test B must be "reseated" or rescheduled for time slots that are available for the complete activity of test B.

For example, in the worklist of Table 1, Test 2 immediately follows Test 1. However, Test 2 cannot be scheduled into the system immediately following Test 1 because they would conflict in Cycle 16 for the R1 delivery time slot. When Test 1 was scheduled, it reserved the R1 delivery slot in Cycle 16. If Test 2 was scheduled right after Test 1, it would have to receive an R1 delivery in Cycle 16 at the same time slot occupied by Test 1 which would create a conflict. Therefore, the next assay, Test 3, is scheduled right after Test 1 to avoid conflicts with Test 1, and Test 2 is scheduled right after Test 3.

One of the advantages of variable timing of the incubation periods is that samples which could have relatively short incubation periods might languish in clinical analysis systems having fixed incubation durations for all assays. With variable timing of incubation periods as disclosed herein samples with relatively short incubation can be run simultaneously with assays having longer incubation periods. A further advantage is that samples which are brought to the clinical analyzer during operation of the analyzer can be scheduled for processing in open time slots in the Table 3—Cycle Event Table, without interfering with tests that are already scheduled in the Table 3—Cycle Event Table.

Once the timing parameters of each of the seven tests of Table 2 have been scheduled without conflict, as on the Table 3—Cycle Event Table, the sequence of testing for Tests 1 through 7 can be determined. Thus based on the Table 3—Cycle Event Table it is determined that a conflict will occur if Tests 1-7 are run in the sequence of their test numbers. The Table 3—Cycle Event Table will show that a non-conflict testing sequence should be Test 1, Test 3, Test 2, Test 6, Test 4, Test 5 and Test 7.

After the non-conflict test sequence is established, a cuvette position in the cuvette ring 102 for each test can be determined as indicated in the following Ring Table (Table 4).

TABLE 4

| Time Cycle Number | Ring Test Sequence | Overall Number of Time Cycles | Cuvette Position on Ring |
|---|---|---|---|
| 1 | Test 1 | 56 | 25 |
| 2 | Test 3 | 31 | 49 |
| 3 | Test 2 | 56 | 23 |
| 4 | Test 6 | 20 | 58 |
| 5 | Test 4 | 20 | 57 |
| 6 | Test 5 | 40 | 36 |
| 8 | Test 7 | 41 | 33 |

Cuvette location or position in the cuvette ring 102, as indicated in Table 4, is based on the number of time cycles that must elapse before the overall number of incubation time cycles, as indicated in Table 2—Test Definitions—Timing Parameters are completed for each of the seven tests.

It is a known requirement of clinical analyzers employing ring movement of cuvettes and a read operation, that after the overall incubation periods are completed for each test, the fully incubated cuvette must be located in the cuvette ring at a position that registers with the read position.

Thus in the clinical analyzer 100 when the fully incubated cuvette arrives at and registers with the read position, namely the reference position 80a, an elevator or ejection mechanism (not shown) ejects the fully incubated cuvette upwardly from the cuvette ring 102 into the luminometer 140 (FIG. 1), which is accessible at the reference position 80a on the fixed surface 200.

Since the luminometer read position is at the reference position 80a on the fixed surface 200, the position of the cuvette ring 102 for a particular assay is determined by subtracting the overall number of time cycles for a particular test and the number of sequential cycles before sample dispensation from 80, then adding one as indicated in the following formula.

Ring position For a Particular Assay=80−(overall number of cycles for that assay+cycle sequence number)+2(if the resulting value is less than 1, multiples of 80 are added to bring the value within the range of 1 to 80)

As indicated in Table 2—Test Definitions—Timing Parameters, the Test 1 cuvette has an overall incubation period of 56 time cycles before it enters the luminometer 140. Thus since the luminometer 140 (FIG. 1) is accessible at the reference position 80a (FIG. 5) on the fixed surface 200 of the clinical analyzer 100, the Test 1 cuvette must be 56 time cycles or 56 cuvette positions away from the luminometer reference position 80a on the fixed surface 200, including the cuvette position itself. Therefore the Test 1 cuvette, after it receives sample must be at the reference position 25a (FIG. 5) of the fixed surface 200 of the clinical analyzer 100.

For purposes of facilitating the description of movement of the cuvette ring 102, the cuvette ring 102 is oriented in FIG. 5 such that the numbered cuvettes as indicated by the numerical indicia on the movable cuvette ring 102 register with the corresponding numbered reference positions as indicated by the numerical indicia on the fixed surface 200 of the clinical analyzer 100.

It will be assumed that the position of the cuvette ring 102 in FIG. 5 at the end of the first cycle is the incremented position for the first cycle. It will be noted that the test cuvettes 23, 25, 33, 36, 49, 57 and 58 are each distinctly identified in the cuvette ring 102 for FIGS. 5-19. However these cuvettes do not receive sample or reagent until the cycles specifically indicated in the Table 3—Cycle Event Table as will be described herein.

In order for the Test 1 cuvette (cuvette 25) to receive sample the cuvette ring 102 (FIG. 5) must rotate to bring the Test 1 cuvette to the sample dispense port 114 (FIG. 3) in the cover tray 110 to receive sample. The sample dispense port 114 corresponds to the reference position 10a (FIG. 5) on the fixed surface 200. After sample is dispensed into the Test 1 cuvette, the cuvette ring 102 rotates fifteen cuvette positions in a counterclockwise direction to return to its incremented position, which registers with the reference position 25a on the fixed surface 200.

It should also be noted that the Test 1 cuvette 25 can be moved to the sample dispense reference position 10a (FIG. 5) on the fixed surface 200 by rotating the cuvette ring 102 counterclockwise from the reference position 25a on the fixed surface 200 to the reference position 10a on the fixed surface 200, which is a distance of sixty-five cuvette spaces. However the cuvette ring 102 is preferably programmed to rotate in a direction that results in the smallest ring movement to get to a particular destination, to save time. Thus the cuvette ring 102 will be programmed to rotate the Test 1 cuvette fifteen cuvette positions clockwise rather than sixty-five cuvette positions counterclockwise to reach the sample dispense port reference location 10a on the fixed surface 200, to receive sample dispensation.

For purposes of clarity the cover tray 110 of FIG. 3 is not shown in any of the FIGS. 5-19. However it should be noted that the sample dispense port opening 114 in the cover tray 110 of FIG. 3 corresponds to the sample dispense reference position 10a on the fixed surface 200 of FIGS. 5-19. Also the reagent dispense port opening 116 of the cover tray 110 in FIG. 3 corresponds to the reagent dispense reference position 20a on the fixed surface 200 of FIGS. 5-19.

As previously indicated, the cover tray 110 (FIG. 3) does not rotate with the underlying cuvette ring 102 (FIGS. 5-19). Therefore the sample dispense port opening 114 (FIG. 3) and the reagent dispense port opening 116 in the cover tray 110 are always aligned with the sample dispense reference position 10a and the reagent dispense reference position 20a on the fixed surface 200 of FIGS. 5-19. Under this arrangement cuvettes in the cuvette ring 102 can only receive sample when a test cuvette in the cuvette ring 102 aligns with the sample dispense reference position 10a on the fixed surface 200 of the clinical analyzer as shown in FIGS. 5-19.

Furthermore, a test cuvette in the cuvette ring 102 can receive reagent through the reagent dispense port 116 (FIG. 3) of the cover tray 110 only when the test cuvette in the cuvette ring 102 aligns with the reagent dispense reference position 20a on the fixed surface 200 of FIGS. 5-19. Cuvettes in the cuvette ring 102 that do not align with the sample dispense reference position 10a on the fixed surface 200 or the reagent dispense reference position 20a on the fixed surface 200 cannot receive sample or reagent.

Thus in order to receive sample or reagent, a cuvette in the cuvette ring 102 must register with the sample dispense reference position 10a on the fixed surface 200 of the clinical analyzer or the reagent dispense reference position 20a on the fixed surface 200 of the clinical analyzer.

As indicated in Table 2—Test Definitions, the cuvette for Test 3, which is the second sequential test in Table 3—Cycle Event Table, has an overall incubation time of thirty-one time cycles before it is subject to a read operation in the luminometer 140. Therefore the Test 3 cuvette, after it receives sample, must be in a cuvette position that is thirty-one cuvette positions from the luminometer read reference position 80a, including the cuvette position itself.

However sample dispensation can occur only once per time cycle because, as shown in the Cycle Timing of FIG. 4, sample dispensation takes up slightly more than eleven seconds of the twenty second cycle time. Thus, the Test 3 cuvette cannot receive sample during the same first cycle when sample is dispensed to the Test 1 cuvette. Therefore the Test 3 cuvette must receive sample during the next cycle, namely the second cycle. The Test 3 cuvette is thus positioned in the cuvette ring 102 at cuvette position 49 (FIG. 6).

Under this arrangement the Test 3 cuvette (sequence 002 of Table 3—Cycle Event Table) is scheduled to arrive at reference position 50a on the fixed surface 200 of the clinical analyzer in the second time cycle wherein cuvette position 49 registers with the reference position 50a of the fixed surface 200.

Thus during the second time cycle, sample is dispensed into the Test 3 cuvette which is located at cuvette position 49 (FIG. 6). Sample is dispensed into the Test 3 cuvette during the time cycle when the Test 3 cuvette arrives at reference position 50a, thirty-one time cycles or thirty-one cuvette positions away from the luminometer read station at reference position 80a on the fixed surface 200, including the cuvette position itself.

At the end of cycle 1, cuvette position 49 registers against reference position 49a on the fixed surface 200. At 4 seconds into cycle 2 the ring indexes to its incremented position to register cuvette 49 against reference position 50a. In order for the Test 3 cuvette (cuvette 49) to receive sample the cuvette ring 102 (FIG. 6) rotates clockwise from the reference position 50a on the fixed surface 200, a distance of forty cuvette spaces to the sample dispense port reference position 10a on the fixed surface 200 where sample is dispensed into the Test 3 cuvette. The Test 3 cuvette is then rotated in a counterclockwise direction forty cuvette spaces by the cuvette ring 102 to return to its incremented position wherein the cuvette 49 on the cuvette ring 102 registers with the reference position 50a on the fixed surface 200.

Since the Test 3 cuvette (cuvette 49) must move from the reference position 50a on the fixed surface 200 to the reference position 10a on the fixed surface 200 to receive sample dispensation, it is equidistant (forty cuvette spaces) from the sample dispense reference position 10a on the fixed surface 200, whether the cuvette ring 102 rotates clockwise or counterclockwise. Therefore there is no preferred direction of shortest distance choice to dictate whether the cuvette ring 102 should rotate clockwise or counterclockwise to obtain sample dispensation to cuvette 49.

The cuvette ring 102 can thus be programmed to move in a selected clockwise or counterclockwise direction to the sample dispense port reference position 10a when there is no preferred shortest distance direction to the sample dispense reference position 10a.

Figure 7:
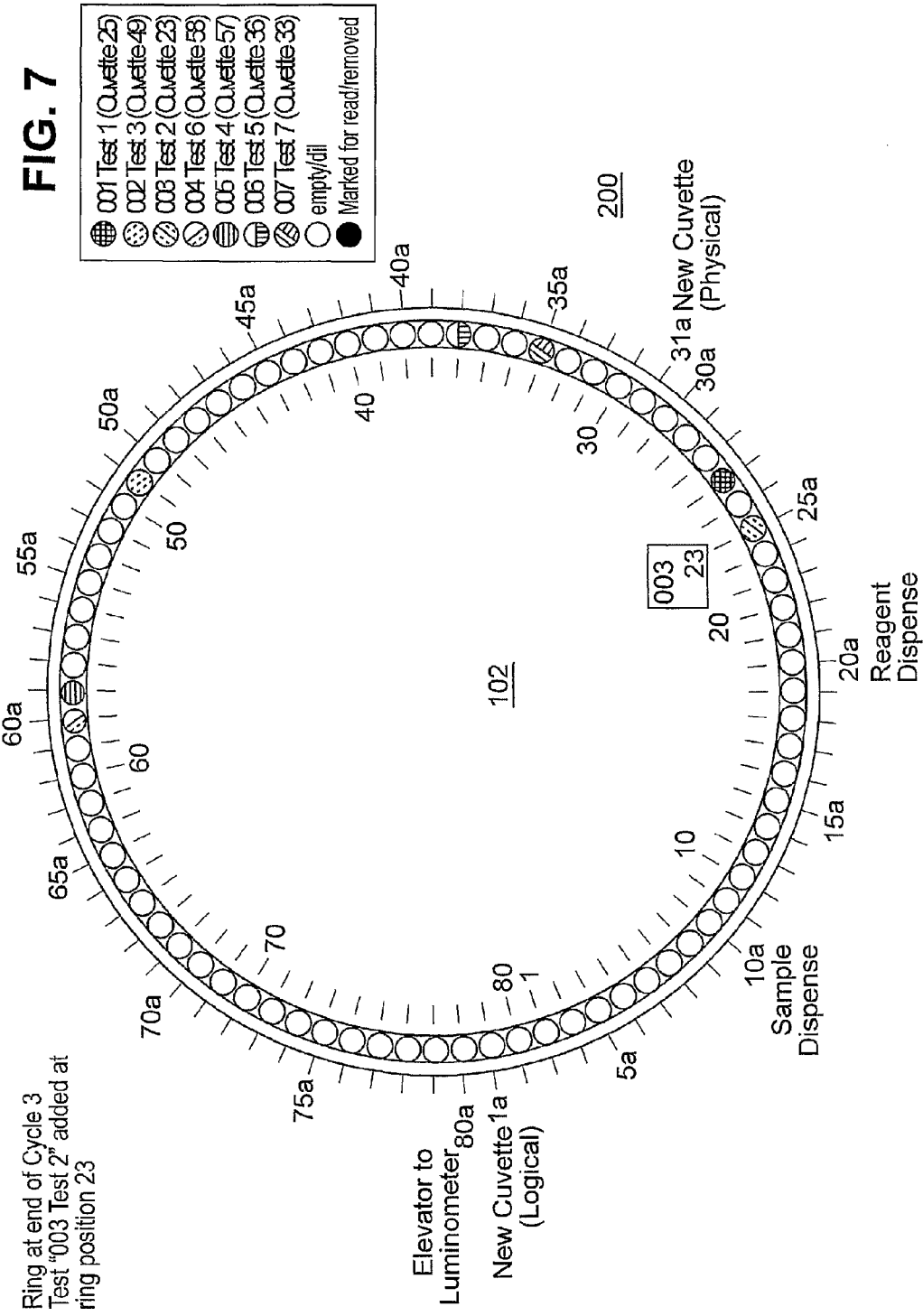

As indicated in Table 2—Test Definitions the assay of Test 2 has an overall incubation time of fifty-six cycles. The assay of Test 2 is scheduled to occur third in sequence as indicated on the Table 3—Cycle Event Table. Therefore the Test 2 cuvette (sequence 003 of Table 3—Cycle Event Table) is positioned in the cuvette ring position 23 (FIG. 7). The cuvette position 23 on the cuvette ring 102 (FIG. 7) will register with the reference position 25a on the fixed surface 200 at the end of the third time cycle (FIG. 7).

Under this arrangement the Test 2 cuvette (sequence 003 of Table 3—Cycle Event Table) is scheduled to arrive at reference position 25a on the fixed surface 200 during the third time cycle. The Test 2 cuvette at position 23 on the cuvette ring 102 is ready to receive sample during the time cycle when it is fifty-six counterclockwise cuvette spaces away from the luminometer read station at reference position 80a on the fixed surface 200, including the cuvette position itself.

At the end of cycle 2, cuvette position 23 registers against reference position 24a on the fixed surface 200. At 4 seconds into cycle 2 the ring indexes to its incremented position to register cuvette 23 against reference position 25a. In order for the Test 2 cuvette (cuvette 23) to receive sample dispensation the cuvette ring 102 (FIG. 7) rotates in a clockwise direction fifteen cuvette positions, to the sample dispense port reference position 10a on the fixed surface 200 to align cuvette 23 with the sample dispense reference position 10a. The cuvette ring 102 then rotates the Test 2 cuvette (cuvette 23)(FIG. 7) in a counterclockwise direction the same number of cuvette positions to return to its incremented position wherein cuvette 23 in the cuvette ring 102 is aligned with the reference position 25a on the fixed surface 200.

The cuvette ring 102 can also theoretically rotate the cuvette 23 in a counter-clockwise direction a distance of sixty-five cuvette spaces to reach the sample dispense port reference position 10a on the fixed surface 200. Since cuvette ring rotation is programmed to move in the direction of shortest distance to the sample dispense port reference position 10a on the fixed surface 200, the cuvette ring 102 will rotate clockwise the fifteen cuvette positions to the sample dispense port reference position 10a. It will also be noted that the cuvette 25 (Test 1)(FIG. 7) has incremented to the fixed surface reference position 27a and the cuvette 49 (Test 3) has incremented to the fixed surface reference position 51a.

Figure 8:
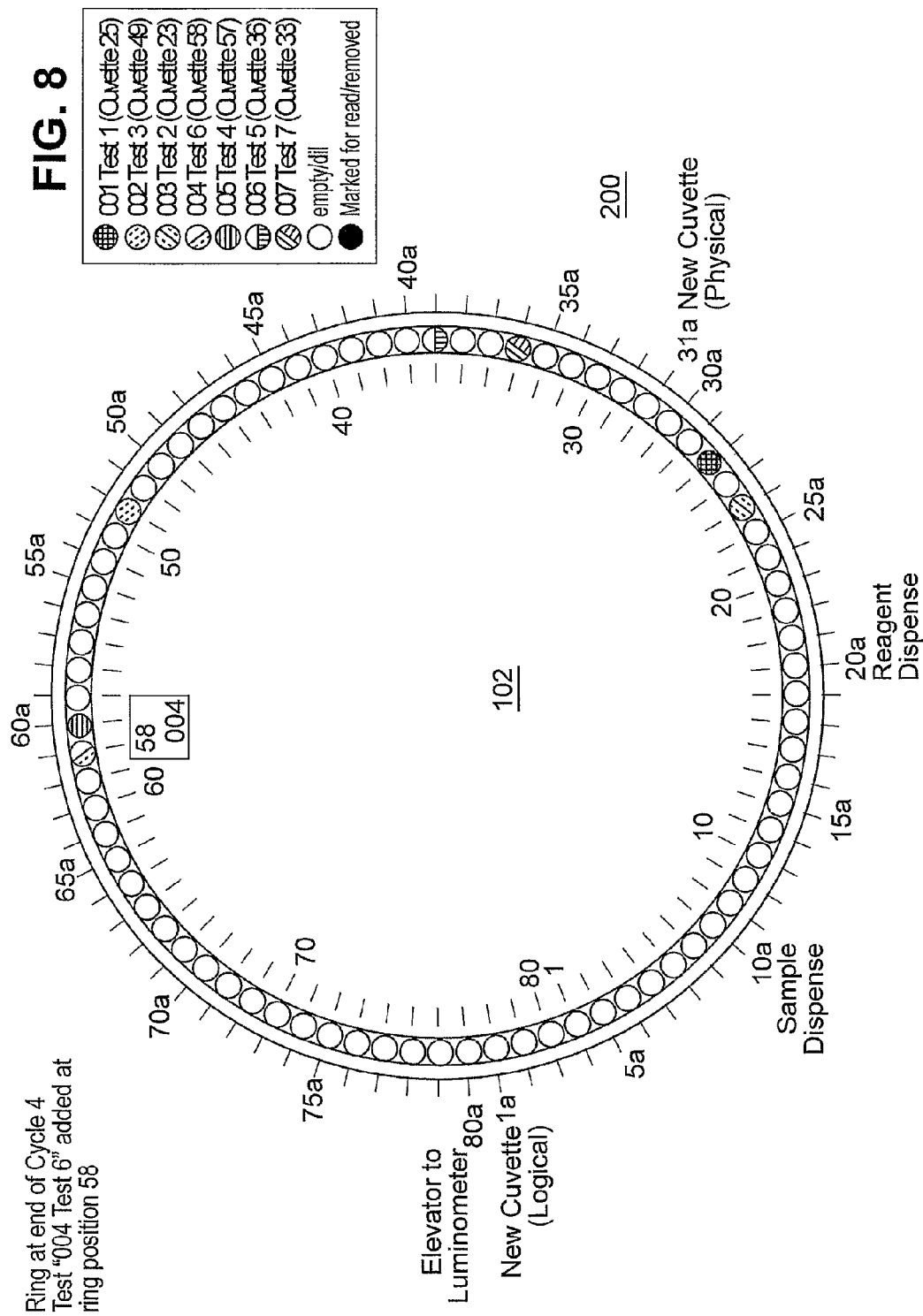

The fourth sequential assay as indicated on the Table 3—Cycle Event Table is the assay of Test 6 (sequence 004) which has an overall incubation period of twenty time cycles. However since the Test 6 cuvette (cuvette 58) must wait 4 cycles before it receives sample and thus progressively moves in four incremental steps four cuvette spaces until it receives sample, its position in the cuvette ring 102 is cuvette position 58 (FIG. 8). As noted in FIG. 8 the cuvette ring position 58 registers with the reference position 61a on the fixed surface 200 at the end of the 4$^{th}$ cycle and is therefore twenty cuvette spaces away from the luminometer including the cuvette position itself. In order to receive sample, the cuvette ring 102 needs to rotate twenty-nine positions counterclockwise to bring cuvette 58 to the sample dispensation port reference position 10a on the fixed surface 200. After sample dispensation, the cuvette ring 102 is rotated clockwise twenty-nine positions to its incremented position for that cycle.

The cuvette 58 (Test 6) (FIG. 8) can also receive sample by rotating the cuvette ring 102 clockwise fifty-one cuvette positions to the sample dispense port reference position 10a on the fixed surface 200. Since the cuvette ring 102 is programmed to take the direction of shortest distance to the sample dispense port reference position 10a on the fixed surface 200, the cuvette ring 102 will rotate counter-clockwise twenty-nine cuvette positions to the sample dispense port reference position 10a. It will also be noted that the cuvette in the ring position 23 (Test 2) (FIG. 8) has incremented to the reference position 26a, the cuvette in the ring position 25 (Test 1) has incrementally moved to the reference position 28a and the cuvette in the ring position 49 (Test 3) has moved incrementally to the reference position 52a.

Figure 9:
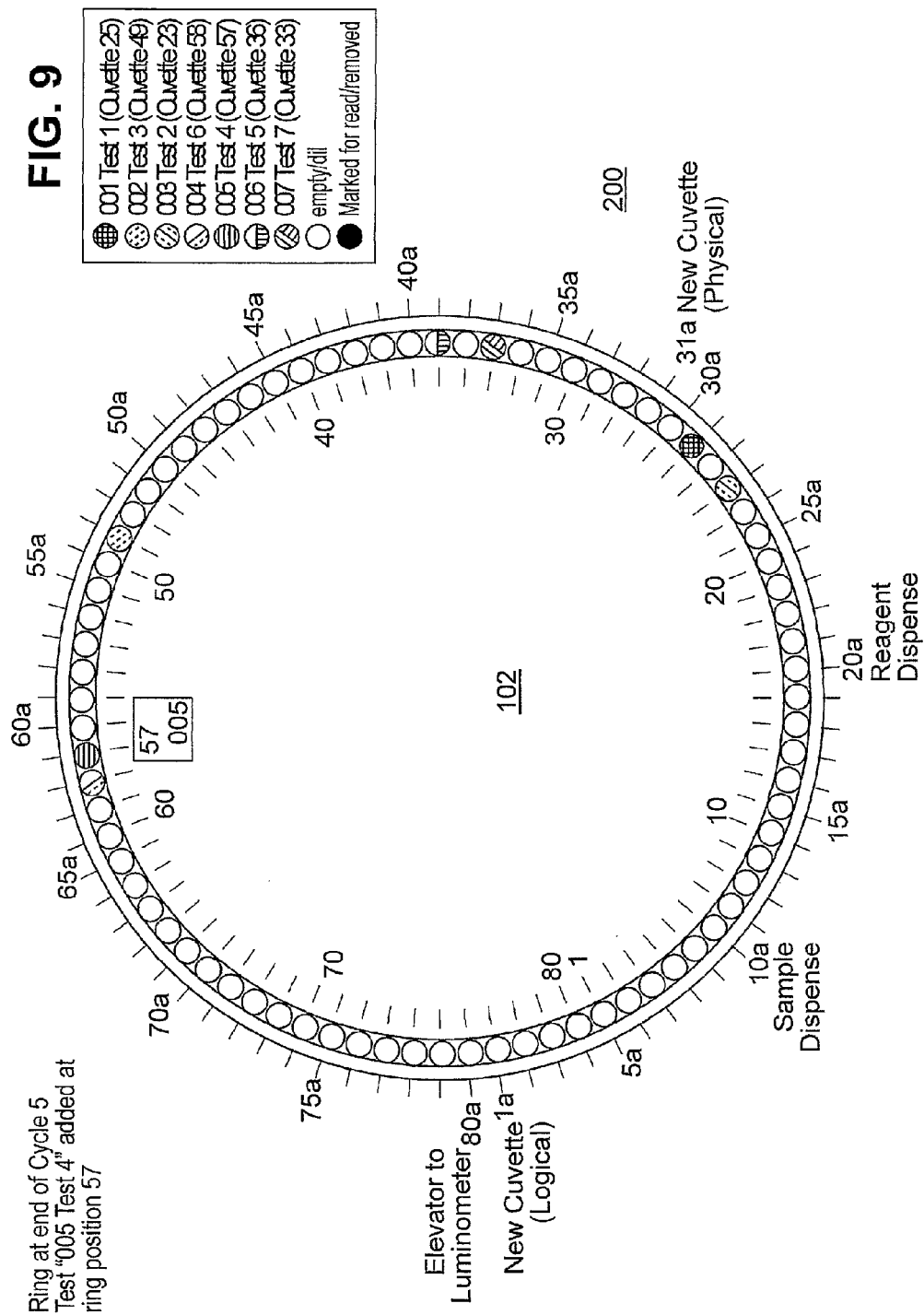

FIG. 9 shows the position of the cuvette ring 102 corresponding to the end of the fifth cycle. Thus sample dispensation is made to the cuvette 57 (Test 4—sequence 005) during the time cycle when it has incrementally moved to the reference position 61a on the fixed surface 200.

Figure 10:
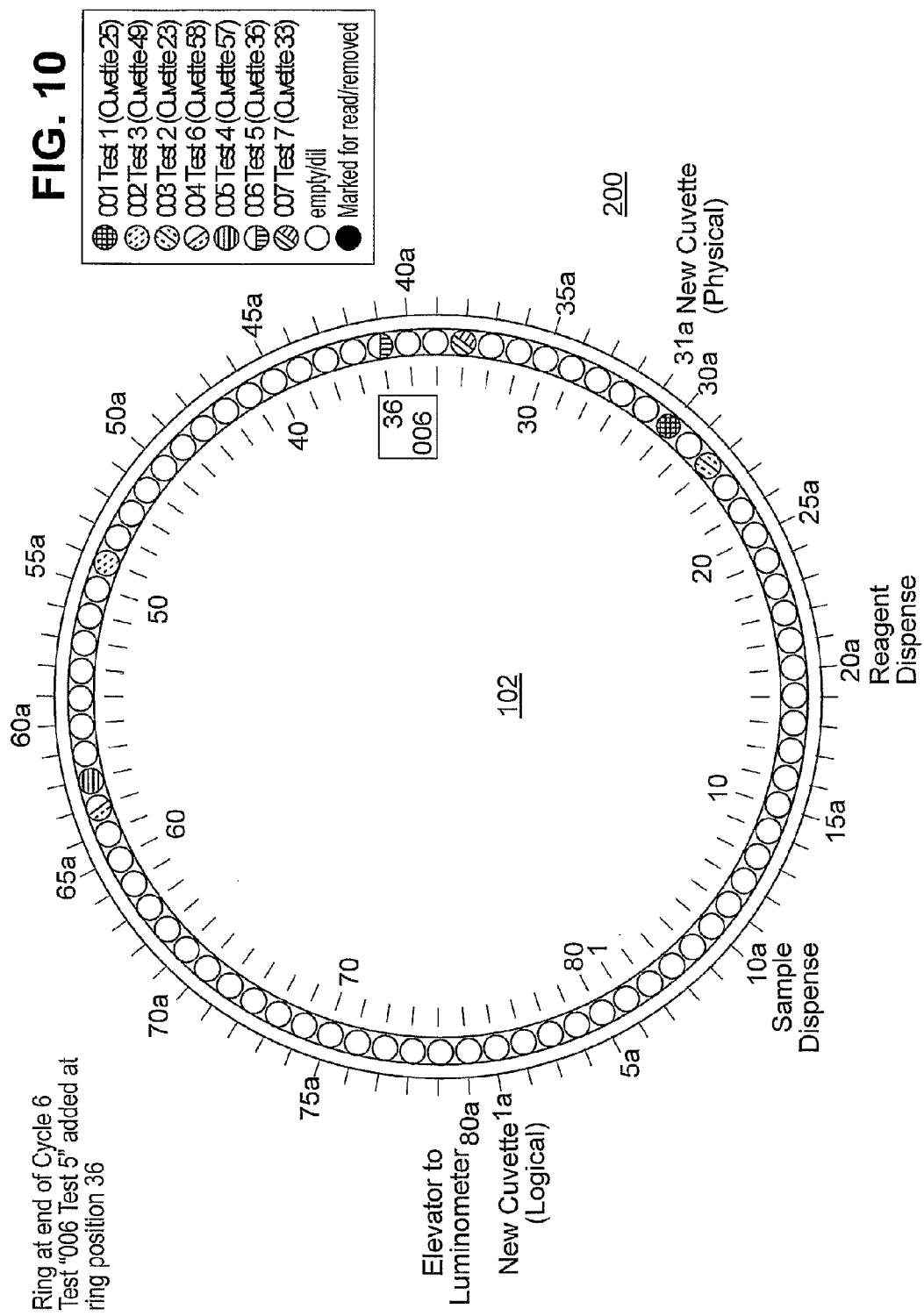

FIG. 10 corresponds to the position of the cuvette ring 102 at the end of sixth cycle. Thus sample dispensation is made to the cuvette 36 (Test 5—sequence 006) during the time cycle when cuvette 36 has incrementally moved to the reference position 41a on the fixed surface 200.

As previously noted, each sample dispensation must always occur at the sample dispense port 114 (FIG. 3) of the cuvette cover tray 110, which sample dispense port 114 is at the reference position 10a on the fixed surface 200. Thus the cuvette ring 102 must rotate a selected amount within a particular time cycle to move the particular cuvette needing sample dispensation to the sample dispense port reference position 10a and then return within the same time cycle to the original incremented position of the cuvette ring 102 for that same time cycle.

It is apparent from the description of sample dispensation for the Tests 1-6 that the cuvette ring 102 may rotate different amounts during any given time cycle to dispense sample at a time cycle that provides for incubation durations as detailed in the Table 2—Test Definitions Table and the Table 3—Cycle Event Table.

The Table 3—Cycle Event Table shows a dilution process in cycle 7. A dilution consists of adding sample and diluent (from the ancillary tray 182 in FIG. 1) into an empty cuvette in one time cycle. In the next time cycle, the diluted sample is aspirated from the dilution cuvette instead of from the sample tube 164 in FIG. 1, and then dispensed into a new cuvette as previously described. One of the advantages of this invention, due to the ability to perform variable ring movement, is that any cuvette on the cuvette carrier can be used for a dilution process rather than requiring that a cuvette be in a particular sequence.

To perform a dilution, sample is dispensed into an empty cuvette that is brought to the sample dispense port reference position 10a in a variable move from its current location. The cuvette is then moved to the reagent dispense port reference position 20a by a counterclockwise move of 10 positions to receive diluent by the reagent probe. In the next cycle, this cuvette is brought by a variable move from its current location to the sample dispense port reference position 10a to aspirate the diluted sample. Next, the cuvette of the target assay is brought to the sample dispense port reference position 10a for dispensing the diluted sample into it as previously described. The diluted sample is scheduled to receive reagents and undergo wash and read operations like a routine sample in accordance with the principles previously described.

Figure 11:
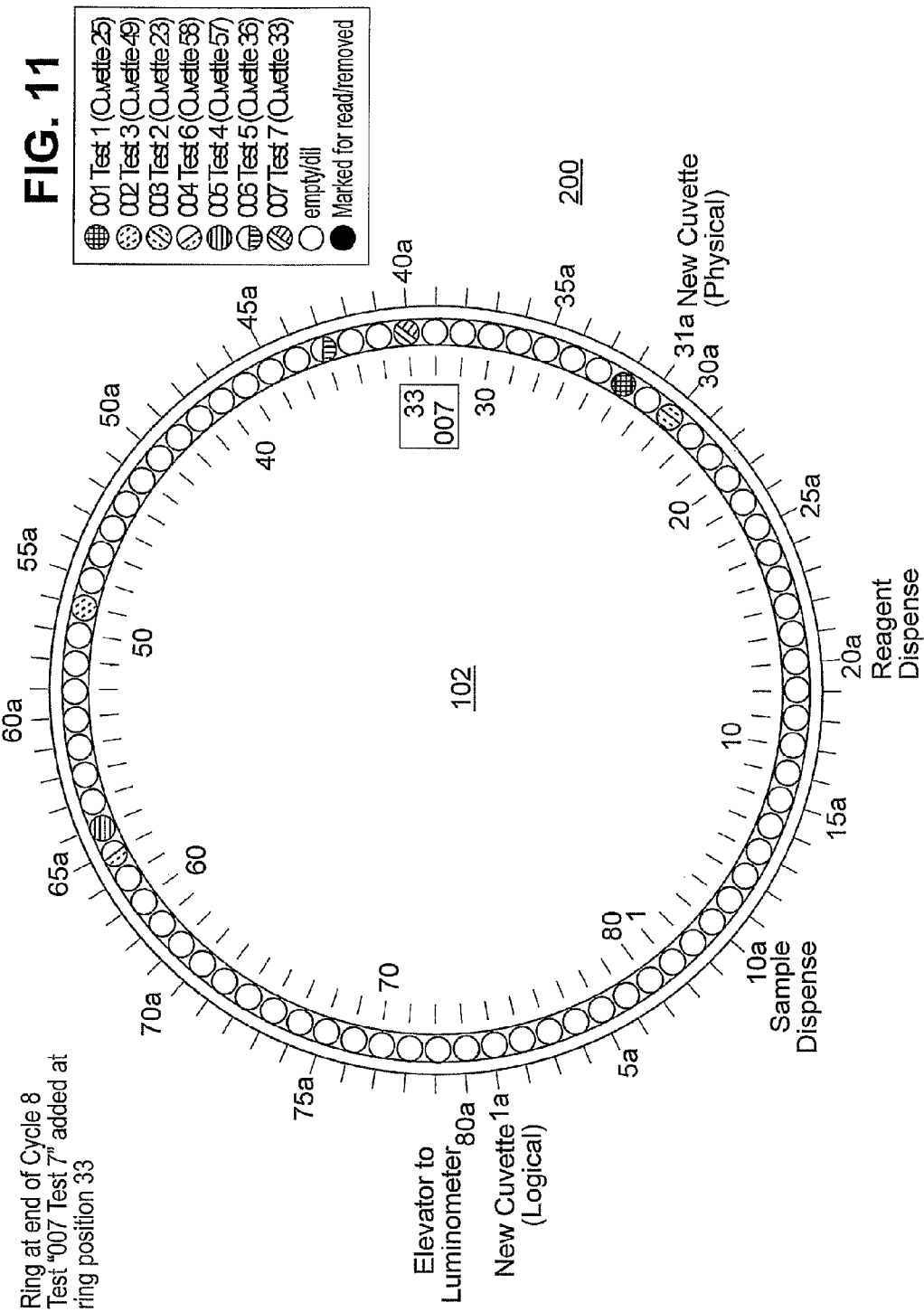

As indicated in the Table 3—Cycle Event Table, sample dispensation for Test 7 takes place during the 8$^{th}$ time cycle (FIG. 11). At the end of eighth time cycles the cuvette 33 (Test 7—sequence 007) in the cuvette ring 102 arrives, via incremental movement to the reference position 40a on the fixed surface 200 after having sample dispensed into it.

Figure 12:
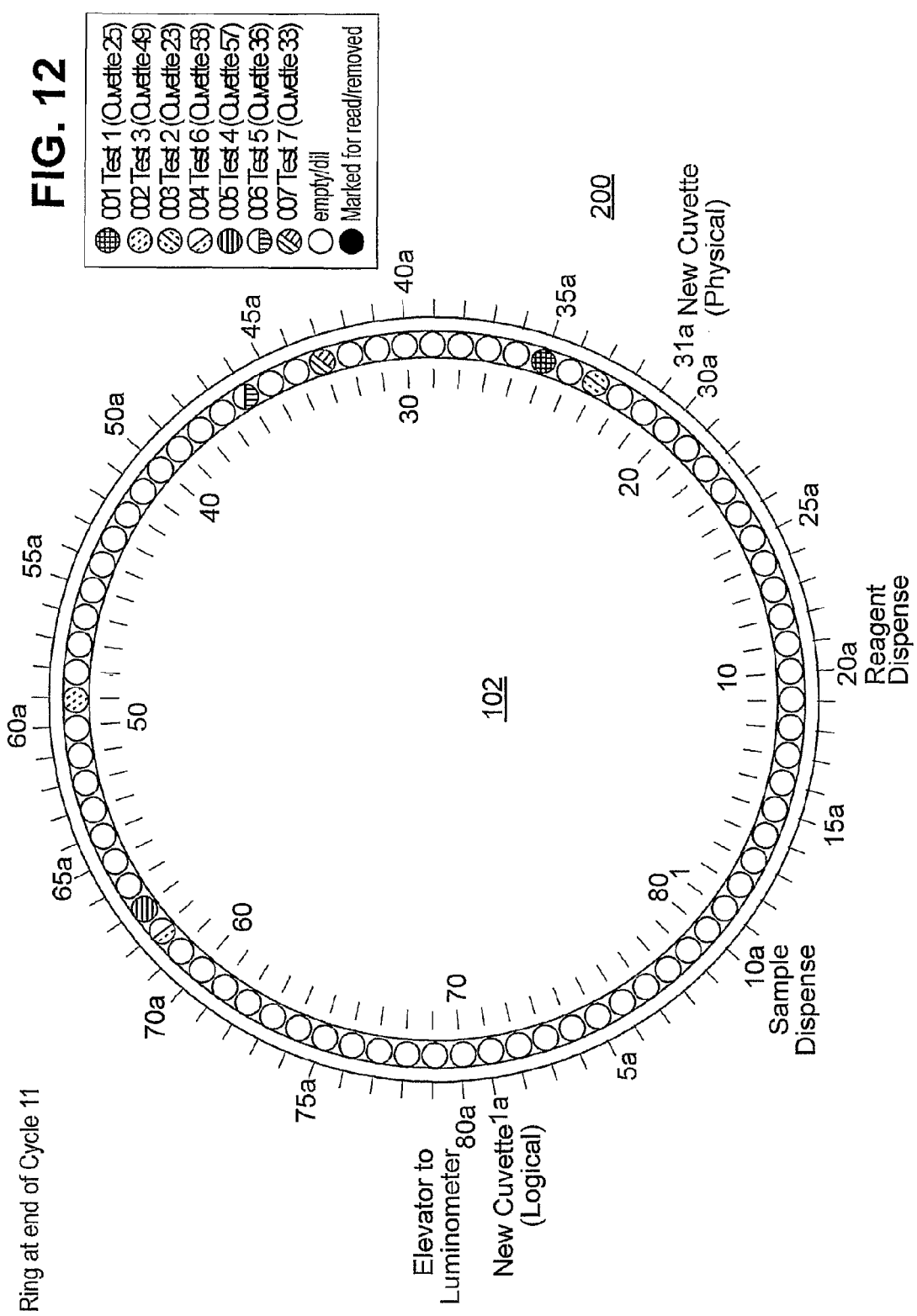

FIG. 12 shows the position of the cuvette ring 102 at the end of the 11$^{th}$ time cycle. As indicated in the Table 3—Cycle Event Table, on the 12$^{th}$ time cycle the Test 3 cuvette (cuvette 49) on the cuvette ring 102 is scheduled to receive a reagent R1. The Test 3 cuvette (cuvette 49) is at reference position 59a (FIG. 12) on the fixed surface 200.

Figure 13:
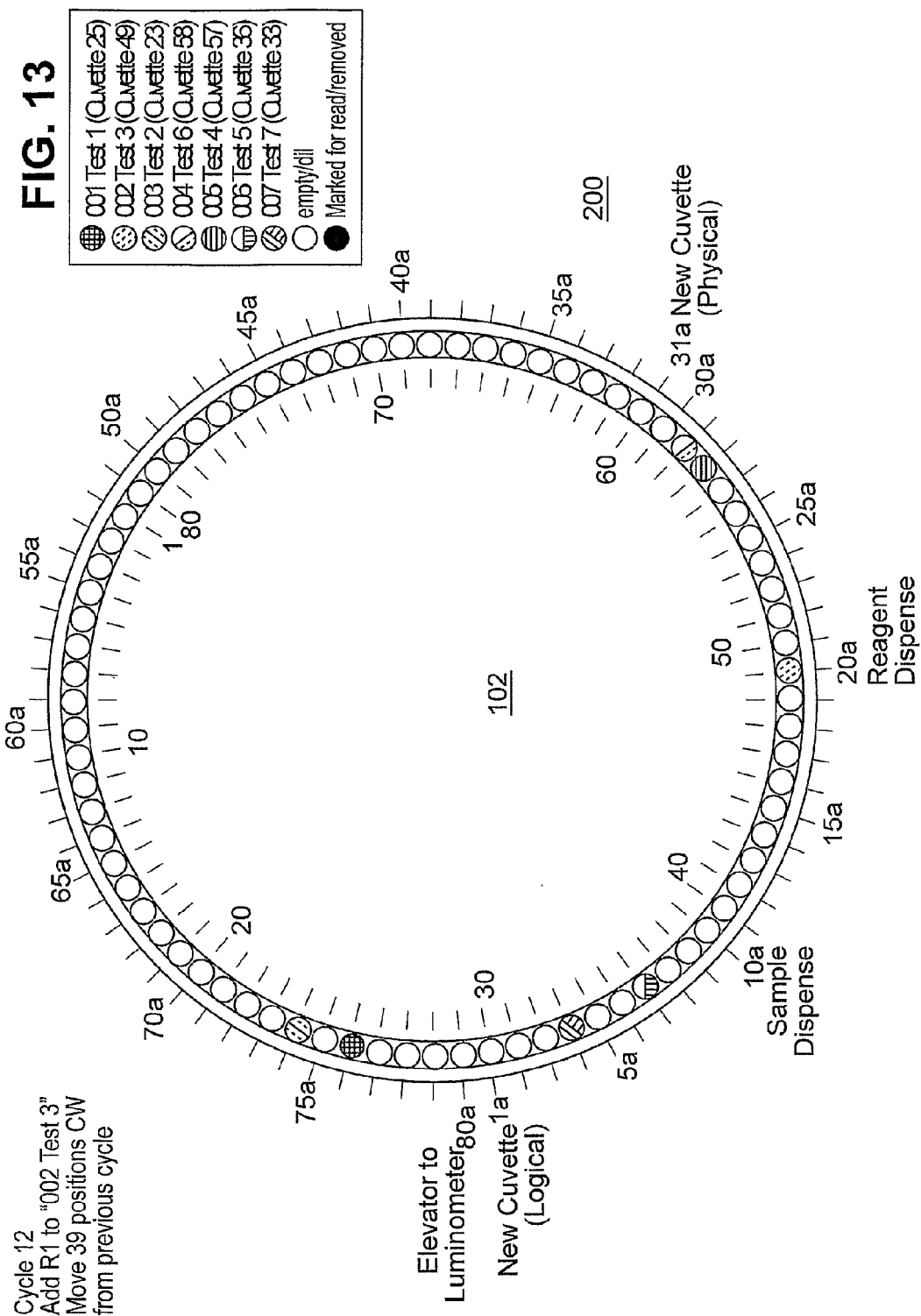
Figure 14:
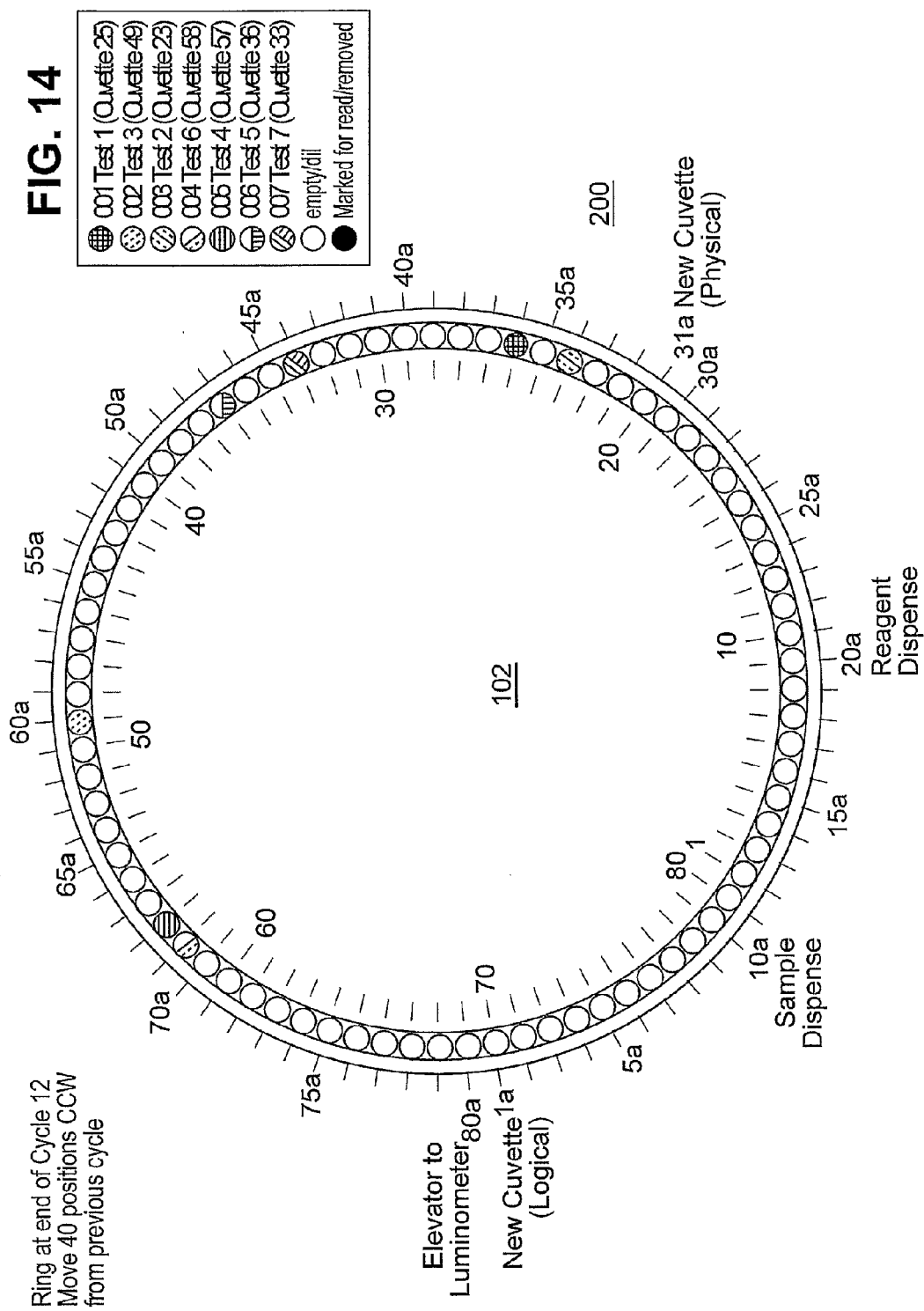

During cycle 12 the cuvette 49 of Test 3 is incrementally moved to the reference position 60a, where it is scheduled to receive reagent R1. Thus the cuvette ring 102 rotates 40 positions in either direction to the reagent dispense port at reference position 20a as shown in FIG. 13, to receive reagent R1. After the cuvette 49 of Test 3 receives reagent R1 the cuvette ring 102 rotates back to its incremented position in cycle 12, before reagent dispensation, to once again align in cycle 12 with the reference position 60a as shown in FIG. 14.

All other cuvettes in the cuvette ring 102 (FIG. 14) that have received sample are likewise incrementally moved an amount corresponding to the twelve incremental cuvette ring movements at the end of the 12$^{th}$ cycle. Thus the cuvette 23 of Test 2 is at the reference position 34a, the cuvette 25 of Test 1 is at the reference position 36a, the cuvette 33 of Test 7 is at the reference position 44a, the cuvette 36 of Test 5 is at the reference position 47a, the cuvette 57 of Test 4 is at the reference position 68a and the cuvette 58 of Test 6 is at the reference position 69a.

Figure 15:
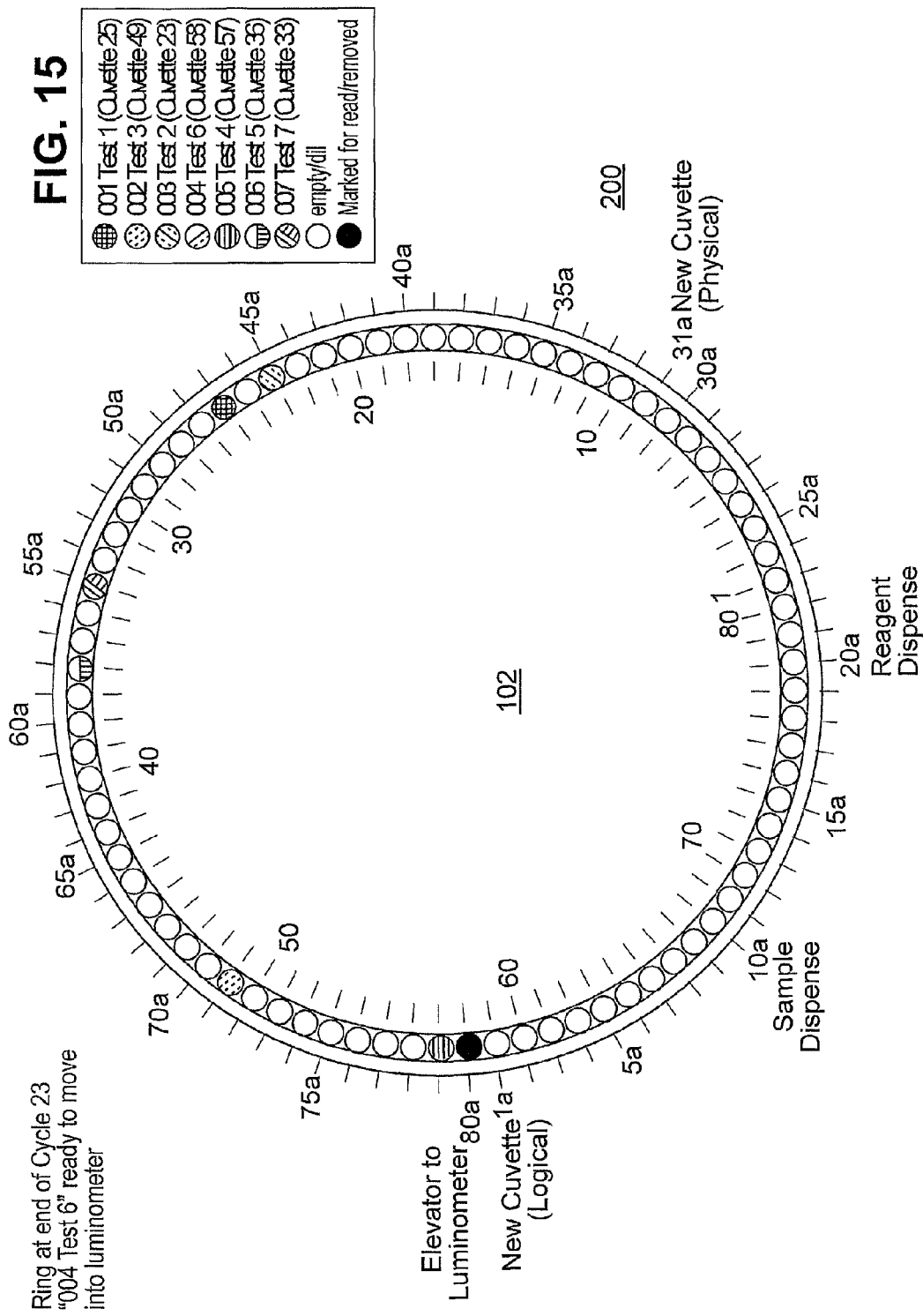
Figure 16:
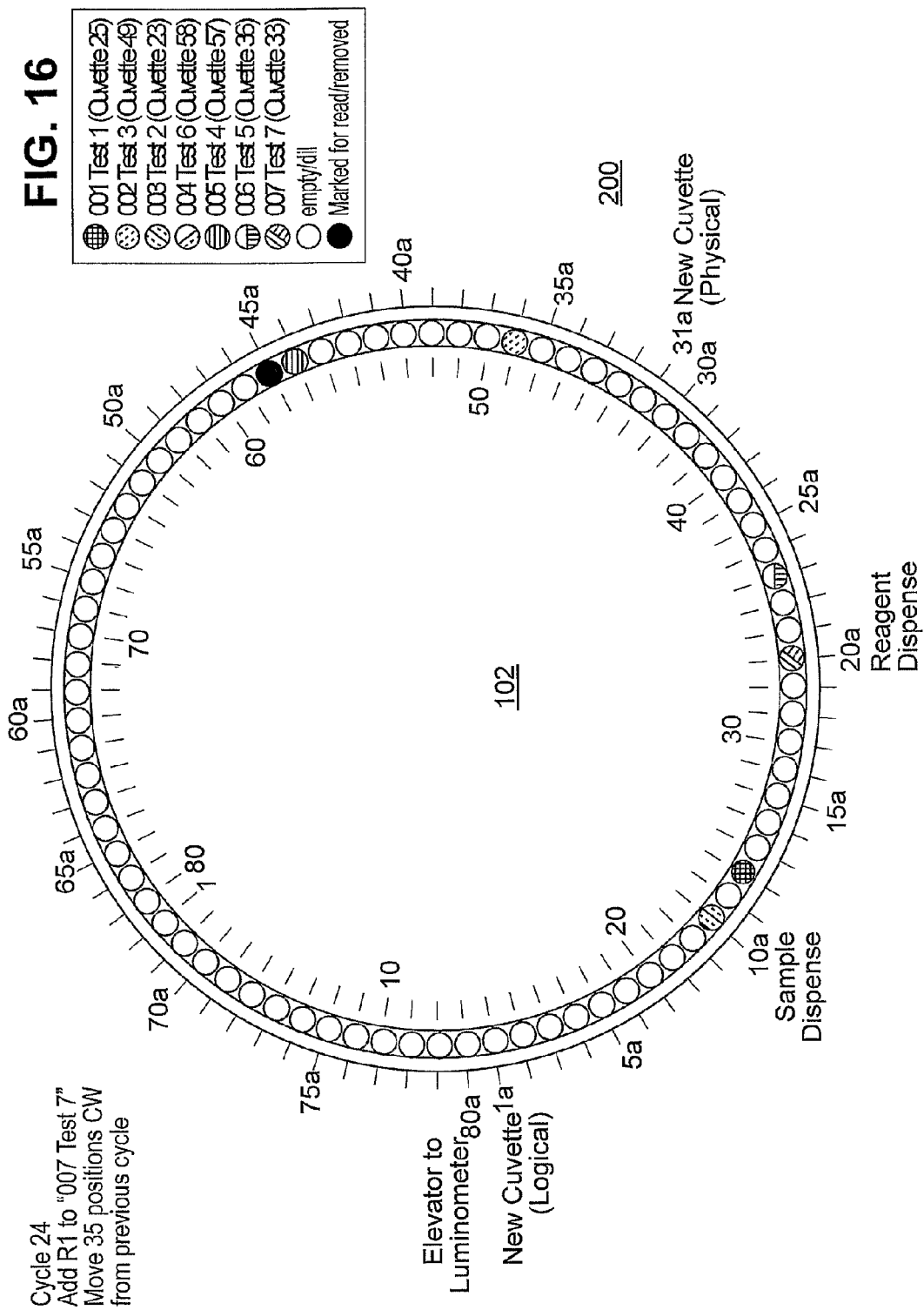

FIG. 15 shows the cuvette ring 102 at the end of time cycle 23. The cuvette 58 of Test 6 on the cuvette ring 102 is at the reference position 80a corresponding to the read position. The cuvette 58 of Test 6 is ready to be elevated or ejected into the luminometer 140 (FIG. 1) for a read function at the beginning of cycle 24. After removal, the cuvette ring 102 (FIG. 15) is thus left with an empty cuvette space at the ring position 58. The ring position 58 is therefore scheduled for installation of a new cuvette during cycle 24 as well, since the read time is early in the cycle and the cuvette installation time is late in the cycle, which allows cuvette replenishment to be carried out in the same cycle.

Referring to the Table 3—Cycle Event Table, four activities take place during the 24$^{th}$ cycle. Test 6 is read, reagent R1 is added to the cuvette of Test 7 (cuvette 33), reagent R2 is added to the cuvette of Test 5 (cuvette 36), and installation of a new cuvette occurs at position 58 of the ring. Also at the end of the 24$^{th}$ cycle the cuvette of Test 4 (cuvette 57) ready to be read in cycle 25.

Thus during the 24$^{th}$ time cycle the cuvette ring 102 will exercise various movements from the end of the cycle 23 position shown in FIG. 15. First, cuvette 58 is elevated into the luminometer 140 for the read operation. The next movement is the regular indexing of the ring, which occurs after 4 seconds into the cycle, followed by a movement of the cuvette ring 102 to bring the cuvette 33 of Test 7 from the reference position 55a (FIG. 15) to the reagent dispense port reference position 20a on the fixed surface 200. Thus the cuvette ring 102 rotates clockwise thirty-five positions to the position shown in FIG. 16.

The next movement of the cuvette ring 162 during cycle 24 is to dispense reagent into the cuvette 36 of Test 5 which is at the reference position 23a (FIG. 16) after reagent is dispensed to the cuvette 33 of Test 7. Thus the cuvette ring 102 moves three positions clockwise from the reference position 23a of FIG. 16 to align with the reference position 20a of FIG. 17 and permit reagent R2 to be dispensed into the cuvette 36.

In the next movement of the cuvette ring 102, the cuvette space 58 is moved by the cuvette ring 102 to the cuvette delivery station at the reference position 31a on the fixed surface 200 to receive a new cuvette as shown in FIG. 18 from the cuvette loader 190 (FIG. 1).

It should be noted that the cuvette loader 190 (FIG. 1) can load a new cuvette into an open space in the cuvette ring 102 only when the open space on the cuvette ring 102 is aligned with the reference position 31a on the fixed surface 200 of the clinical analyzer as shown in FIG. 18. Thus any open space on the cuvette ring 102 must be brought to the reference position 31a on the fixed surface 200 of the clinical analyzer in order to receive a new cuvette. The new cuvette is transferred through the cuvette delivery port 120 (FIG. 3) in the cover tray 110 to the open space 58 (FIG. 18) on the cuvette ring 102 that aligns with the reference position 31a on the fixed surface 200.

It is also feasible to use known cuvettes that are washed in a known manner at the clinical analyzer, and reused in the clinical analyzer.

FIG. 19 shows the position of the cuvette ring 102 at the end of the 24$^{th}$ cycle wherein the cuvette 57 of Test 4 is incremented one position from the position at the end of the 23$^{rd}$ time cycle (FIG. 15). The cuvette 57 of Test 4 (FIG. 19) aligns with the reference position 80a for assay reading wherein the cuvette 57 is ejected into the luminometer 140 at the beginning of the 25$^{th}$ time cycle.

The Table 3—Cycle Event Table for the 24$^{th}$ time cycle thus indicates four different activities. Each of the activities involves a movement of the cuvette ring 102 a variable amount during time cycle 24 to accomplish the required functions. At the end of the 24$^{th}$ time cycle (FIG. 19) the cuvette ring 102 returns to its incremented position relative to the fixed surface 200.

Thus before the end of each time cycle the cuvette ring 102 will always return to its incremented position after previously moving variable clockwise and counterclockwise amounts to accomplish the individual and plural functions scheduled for the cuvette ring in Cycle Event Table (Table 3).

The following principles summarize the Ring Positioning Logic, Ring Movement Logic and Conflict Management Logic.

New Cuvette Positioning Logic

In every cycle, there is a time slot where one of the cuvettes is moved to the read station (reference position 80a). The cuvette ring 102 increments by one position counterclockwise in every cycle. At the end of cycle 1, ring position 1 is at the work surface reference position 1a. In cycle 2, ring position 80 is at work surface reference position 1a, etc. The cuvette into which sample and reagents are introduced, must arrive at the read station reference position 80 after the number of cycles corresponding to the ("overall" value −1) for that test as defined in the Table 2—Test Definitions Table, so that reading will happen on the following cycle. Using the Table 3—Cycle Event Table, the formula for the cuvette positioning is:

Cuvette position=Ring size minus overall cycles for that test minus cycle number in Cycle Event Table where the test was introduced plus 2. If the resulting value is less than 1, multiples of the ring size are added to bring the value within the range of 1 to the ring size. For example, in Table 4—Ring, for Test 7 starting in cycle 8, the position will be 80−41−8+2=33

Ring Movement Logic

The following is the logic flow for the calculations for the extent and direction of the next variable move:
1. What is the present ring position?
2. What is the next action and which cuvette needs to have this action performed on it?
3. Identify the location where that cuvette needs to go.
   a) Move there, clockwise or counterclockwise.
   b) Take the direction that furnishes the shortest path to the location where the cuvette needs to go.
4. The very last ring move in the time cycle is such that the net change of all the previous moves in that time cycle is one increment position in the chosen direction of incremental movement for the system Conflict Management Logic The following is the logic flow for conflict management:
1. For every new test (or skipped test due to a previous conflict), check that all corresponding Cycle Event Table spots are free.
2. Check if designated cuvette location on cuvette ring is free.
3. If yes to both 1 and 2, make all reservations.
4. If no, scan the Table 1—Worklist Table for all other samples.
   a) Apply logic steps 1 and 2 to every such sample.
   b) If successful, make all reservations for the sample that meet criteria of logic steps 1 and 2. This will result in samples being out of original sequence.
   c) If not, cycle is skipped and return to logic step 1.

It should be noted that the above stated logic is suitable to routine samples. Other considerations may alter it as required. For example, emergency samples may be preferentially scheduled ahead of other samples in life-threatening situations, or calibrators may need to be run ahead of routine samples.

By using known principles of conflict management and known principles of programming the cuvette ring 102 is programmed to perform a discrete set of differing movements during each time cycle. The Table 3—Cycle Event Table for scheduling of activity during each time cycle to avoid conflicts is also established using known programming principles.

As various changes can be made in the above methods without departing from the scope of the invention, it is intended that all matter contained in the above description or shown in the accompanying drawings shall be interpreted as illustrative and not in a limiting sense.

What is claimed is:

1. A method of controlling assay timing in a clinical analyzer that uses discrete reaction cuvettes for each assay, said method comprising,
   (a) identifying the type of test to be made in the clinical analyzer for each desired assay,
   (b) determining the sequence of sample dispensation, reagent dispensation and read operation to be performed for each identified test and a predetermined time duration between each such activity for each identified test that will provide a set of predetermined incubation times for each assay, wherein the predetermined incubation times can be of any selected time duration,
   (c) providing a cuvette carrier that moves cuvettes along a closed geometrical path, the cuvette carrier being configured to alternately couple and decouple to a magnetic segment to provide for selective movement in two opposite directions along the closed geometrical path in order to achieve variable assay incubation timing, wherein the magnetic segment moves with the cuvette carrier when coupled to the cuvette carrier,
   (d) providing a single reagent delivery service station disposed at a fixed reagent delivery location disposed along the closed geometrical path of the cuvette carrier, configured to dispense reagent into a selected cuvette,
   (e) providing a single sample delivery service station disposed at a fixed sample delivery location disposed along the closed geometrical path of the cuvette carrier, configured to dispense sample into a selected cuvette,
   (f) scheduling the sample dispensation, reagent dispensation, and read operation for each assay to allow for the predetermined incubation times for each assay and permit all activities for all assays to be carried out without the operation of one activity interfering with the operation of another activity by checking for each new test that cycle event spots for sample dispensation, reagent dispensation, and read operation of a cycle event schedule are free,
   (g) determining an introductory discrete cuvette position for each assay on the cuvette carrier based on the schedule of activities,
   (h) moving all of the cuvettes on said cuvette carrier in unison, in multiples of incremental steps, along the closed geometrical path, in sequential predetermined time cycles, with incremental movement being made during each time cycle, such that each discretely positioned cuvette progresses to a different, incremented position on the closed geometrical path during each time cycle, and the predetermined incubation times of any time duration are a multiple of the time duration of the predetermined time cycle, wherein the incremental movement is movement of the cuvette carrier of one incremented position on the closed geometrical path,
   (i) when at least one cuvette is scheduled to receive sample in a particular time cycle, moving the one discretely positioned cuvette with the cuvette carrier from the position of the one cuvette in that particular time cycle, to the sample delivery location for sample dispensation, and returning to the same position of the one cuvette in that particular time cycle, and
   (j) when at least one cuvette is scheduled to receive reagent in a particular time cycle, moving the one discretely positioned cuvette with the cuvette carrier to the reagent delivery location for reagent dispensation and returning to the same position of the one cuvette in that particular time cycle,
   wherein variable movement of the cuvette carrier during the particular time cycles provides a variable incubation period.

2. The method of claim 1, including providing a signal reading service station at a fixed signal reading location, on a different plane relative to the closed geometrical path of the clinical analyzer, for reading an assay signal from a cuvette after the predetermined incubation time has elapsed for the assay.

3. The method of claim 2, including transporting a cuvette that has had the predetermined time for incubation, from the cuvette carrier to the signal reading service station at the different plane.

4. The method of claim 3, including providing a cuvette installation service station, at a fixed cuvette installation location relative to the closed geometrical path of the clinical analyzer, for loading a fresh cuvette into a selected cuvette position in the cuvette carrier to replace a cuvette that is removed from the selected cuvette position.

5. The method of claim 1, including providing a separation/wash service station, at a fixed separation/wash service station location relative to the closed geometrical path of the clinical analyzer, for separating/washing components of an assay in a cuvette.

6. The method of claim 1, wherein the step of subparagraph (a) includes establishing a work list indicating the sequential order of receipt of each test and the identification of each test that is to be performed in the clinical analyzer.

7. The method of claim 6, including controlling the operation of the clinical analyzer with a computer and transferring the information of the work list to the computer for programming of such information in the computer controlled operation of the clinical analyzer.

8. The method of claim 1, wherein the step of subparagraph (b) includes establishing a test definitions-timing parameter list or table containing a list of each identified test, the corresponding activities associated with each identified test, and the predetermined time duration or timing parameter between each successive activity of each identified test, that specifies a predetermined set of incubation time for each identified test.

9. The method of claim 8, including indicating the overall predetermined incubation time in the test definitions-timing parameter list or table.

10. The method of claim 8, including controlling the operation of the clinical analyzer with a computer and transferring the information of the test definitions-timing parameter list or table, to the computer for programming of such information in the computer controlled operation of the clinical analyzer.

11. The method of claim 1, including establishing the cycle event schedule indicating each sequential time cycle of the clinical analyzer, identifying the discrete cuvette position of each cuvette on the cuvette carrier that receives a test to be performed in the clinical analyzer, identifying the specific time cycle in which each cuvette that receives a test is to receive sample, identifying the specific time cycle in which each cuvette that receives a test is to receive reagent, and identifying the specific time cycle in which each cuvette that receives a test will be subject to a read operation, to enable one activity to be carried out without interfering with another activity.

12. The method of claim 11, including identifying the specific time cycle in which each cuvette that receives a test is to be subject to a separation/wash operation.

13. The method of claim 11, including identifying the specific time cycle in which a selected test is to be subject to a dilution operation.

14. The method of claim 11, including controlling the operation of the clinical analyzer with a computer and transferring the information of the cycle event schedule to the computer for programming of such information in the computer controlled operation of the clinical analyzer.

15. The method of claim 11, including removing a cuvette from the cuvette carrier when the cuvette is subjected to the read operation, installing a fresh cuvette into the cuvette carrier to replace a cuvette that is removed from the cuvette carrier and identifying the specific time cycle in the cycle event schedule in which the fresh cuvette is installed onto the cuvette carrier to replace the removed cuvette.

16. The method of claim 11, including monitoring the location of every cuvette on the cuvette carrier with respect to a selected fixed reference point relative to the closed geometrical path of the clinical analyzer.

17. The method of claim 16 wherein, if at least one cuvette is scheduled to receive sample or reagent in a particular time cycle, determining the distance of the one cuvette from its current location to the selected sample or reagent delivery location and moving the cuvette carrier in one of the two opposite directions that provide the shortest possible travel path of the one cuvette to the selected sample or reagent delivery location.

18. The method of claim 17 including controlling the operation of the clinical analyzer with a computer and transferring the first direction distance information and the second direction distance information for the one cuvette to the computer for programming of such information in the computer controlled operation of the clinical analyzer, to control movement of the cuvette carrier in the direction of shortest travel to the selected sample or reagent delivery location.

19. The method of claim 2 including providing a wash station, at a fixed wash station location relative to the closed geometrical path of the analyzer, for washing cuvettes after the read operation for reuse in subsequent testing on said clinical analyzer.

20. The method of claim 1 wherein the time duration of a predetermined time cycle is a fixed time duration less than around 30 seconds.

21. The method of claim 1 wherein the closed geometrical path is in the shape of a ring.

* * * * *